US012773430B2

(12) United States Patent
Filutowicz et al.

(10) Patent No.: US 12,773,430 B2
(45) Date of Patent: Oct. 27, 2026

(54) ANTI-BIOFILM AGENTS AND USES THEREOF

(71) Applicant: AmebaGone, LLC, Madison, WI (US)

(72) Inventors: Marcin Filutowicz, Madison, WI (US); Dhanansayan Shanmuganayagam, Madison, WI (US); Nathan James Chesmore, Madison, WI (US)

(73) Assignee: AmebaGone, LLC, Madison, WI (US)

( * ) Notice: Subject to any disclaimer, the term of this patent is extended or adjusted under 35 U.S.C. 154(b) by 433 days.

(21) Appl. No.: 17/237,479

(22) Filed: Apr. 22, 2021

(65) Prior Publication Data

US 2021/0330715 A1 Oct. 28, 2021

Related U.S. Application Data

(60) Provisional application No. 63/014,473, filed on Apr. 23, 2020.

(51) Int. Cl.

| | |
|---|---|
| ***A61K 35/68*** | (2006.01) |
| ***A01N 63/00*** | (2020.01) |
| ***A61P 31/04*** | (2006.01) |

(52) U.S. Cl.

CPC .............. *A61K 35/68* (2013.01); *A01N 63/00* (2013.01); *A61P 31/04* (2018.01)

(58) Field of Classification Search

CPC .......... A61K 35/68; A61P 31/04; A01N 63/00

USPC .......................................................... 424/780

See application file for complete search history.

(56) References Cited

U.S. PATENT DOCUMENTS

| | | | | |
|---|---|---|---|---|
| 4,737,461 A * | 4/1988 | Sugisawa | C12N 1/06 435/259 |
| 8,551,471 B2 | 10/2013 | Filutowicz et al. | |
| 8,715,641 B2 | 5/2014 | Filutowicz et al. | |
| 2010/0305062 A1* | 12/2010 | Onsoyen | A61K 8/733 514/54 |
| 2014/0056850 A1* | 2/2014 | Filutowicz | A01N 63/00 424/93.1 |
| 2019/0110481 A1* | 4/2019 | Sinclair | C09D 7/40 |

FOREIGN PATENT DOCUMENTS

JP WO 2015/029872 * 3/2015

OTHER PUBLICATIONS

Dimond et al., Secretion of Lysosomal Enzymes in the Cellular Slime Mold, *Dictyostelium discoideum*, The Journal of Biological Chemistry, vol. 256, No. 13, (1981), pp. 6565-6572.*

Bakthavatsalam et al., The secreted proteome profile of developing Dictyostelium discoideum cells. Proteomics. Jul. 2010;10(13):2556-9.

Baldauf et al., A kingdom-level phylogeny of eukaryotes based on combined protein data. Science. Nov. 3, 2000;290(5493):972-7.

Banner et al., Localized tufts of fibrils on *Staphylococcus epidermidis* NCTC 11047 are comprised of the accumulation-associated protein. J Bacteriol. Apr. 2007;189(7):2793-804.

Beenken et al., Global gene expression in *Staphylococcus aureus* biofilms. J Bacteriol. Jul. 2004;186(14):4665-84.

Bendy et al., Relationship of Quantitative Wound Bacterial Counts to Healing of Decubiti: Effect of Topical Gentamicin. Antimicrob Agents Chemother (Bethesda). 1964;10:147-55.

Bergstrom et al., Treatment of pressure ulcers. Clinical practice guideline, No. 15. 1994. 20(9); 19-52.

Boles et al., Staphylococcal biofilm disassembly. Trends Microbiol. Sep. 2011;19(9):449-55.

Bowler et al., Wound pathophysiology, infection and therapeutic options. Ann Med. 2002;34(6):419-27.

Branda et al., A major protein component of the Bacillus subtilis biofilm matrix. Mol Microbiol. Feb. 2006;59(4):1229-38.

Branda et al., Biofilms: the matrix revisited. Trends Microbiol. Jan. 2005;13(1):20-6.

Brefeld O. Dictyostelium mucoroides. Ein neuer organismus und der verwandschaft der myxomyceten. Abh Seckenberg Naturforsch Ges. 1869;7:85-107.

Celli et al., Bacterial avoidance of phagocytosis. Trends Microbiol. May 2002;10(5):232-7.

Chiang et al., Extracellular DNA shields against aminoglycosides in Pseudomonas aeruginosa biofilms. Antimicrob Agents Chemother. May 2013;57(5):2352-61.

Conlon. *Staphylococcus aureus* chronic and relapsing infections: Evidence of a role for persister cells: An investigation of persister cells, their formation and their role in *S. aureus* disease. Bioessays. Oct. 2014;36(10):991-6.

Costerton et al., Microbial biofilms. Annu Rev Microbiol. 1995;49:711-45.

Daltrey et al., Investigation into the microbial flora of healing and non-healing decubitus ulcers. J Clin Pathol. Jul. 1981;34(7):701-5.

Davies. Understanding biofilm resistance to antibacterial agents. Nat Rev Drug Discov. Feb. 2003;2(2):114-22.

Davies. Resistance redux. Infectious diseases, antibiotic resistance and the future of mankind. EMBO Rep. Jul. 2008;9 Suppl 1 (Suppl 1):S18-21.

Dunsmore et al., Design and Performance of Systems for Cleaning Product-Contact Surfaces of Food Equipment: A Review. J Food Prot. Mar. 1981;44(3):220-240.

Fey et al., Current concepts in biofilm formation of *Staphylococcus epidermidis*. Future Microbiol. Jun. 2010;5(6):917-33.

Flemming et al., The biofilm matrix. Nat Rev Microbiol. Sep. 2010;8(9):623-33.

Flint et al., Biofilms in Dairy Manufacturing Plant-Description, Current Concerns and Methods of Control. Biofouling 1997; 11:81-97.

Gustilo et al., The management of open fractures. J Bone Joint Surg Am. Feb. 1990;72(2):299-304.

Heidel et al., Phylogeny-wide analysis of social amoeba genomes highlights ancient origins for complex intercellular communication. Genome Res. Nov. 2011;21(11):1882-91.

(Continued)

*Primary Examiner* — Jennifer M. H. Tichy

(74) *Attorney, Agent, or Firm* — Casimir Jones, S.C.; Tanya A. Arenson

(57) ABSTRACT

The present disclosure relates to amoebae (slime molds) and uses thereof. In particular, the present disclosure relates to anti-biofilm components of amoebae to target biofilms.

10 Claims, 6 Drawing Sheets

(56) References Cited

OTHER PUBLICATIONS

Helke et al., Survival and Growth Characteristics of Listeria monocytogenes and *Salmonella typhimurium* on Stainless Steel and Buna-N Rubber. J Food Prot. Nov. 1994;57(11):963-968.
Horn. Food Competition Among the Cellular Slime Molds (*Acrasiea*). Ecology. 1971;52(3):475-84.
Kessler et al., Risk factors for periprosthetic ankle joint infection: a case-control study. J Bone Joint Surg Am. Oct. 17, 2012;94(20):1871-6.
Konijn et al., The acrasin activity of adenosine-3',5'-cyclic phosphate. Proc Natl Acad Sci U S A. Sep. 1967;58(3):1152-4.
Krizek et al., Evolution of quantitative bacteriology in wound management. Am J Surg. Nov. 1975;130(5):579-84.
Kumar et al., Significance of microbial biofilms in food industry: a review. Int J Food Microbiol. Jun. 30, 1998;42(1-2):9-27.
Laffer et al., Outcome of prosthetic knee-associated infection: evaluation of 40 consecutive episodes at a single centre. Clin Microbiol Infect. May 2006;12(5):433-9.
Li et al., Conversion of *Staphylococcus epidermidis* strains from commensal to invasive by expression of the ica locus encoding production of biofilm exopolysaccharide. Infect Immun. May 2005;73(5):3188-91.
Lynch et al., Bacterial and fungal biofilm infections. Annu Rev Med. 2008;59:415-28.
Mah et al., Mechanisms of biofilm resistance to antimicrobial agents. Trends Microbiol. Jan. 2001;9(1):34-9.
Massey et al., Phenotypic switching of antibiotic resistance circumvents permanent costs in *Staphylococcus aureus*. Curr Biol. Nov. 13, 2001;11(22):1810-4.
Massey et al., Antibiotic-resistant sub-populations of the pathogenic bacterium *Staphylococcus aureus* confer population-wide resistance. Curr Biol. Oct. 15, 2002;12(20):R686-7.
Matz et al., Off the hook—how bacteria survive protozoan grazing. Trends Microbiol. Jul. 2005;13(7):302-7.
More et al., Extracellular polymeric substances of bacteria and their potential environmental applications. J Environ Manage. Nov. 1, 2014;144:1-25.
Murdoch et al., Infection of orthopedic prostheses after *Staphylococcus aureus* bacteremia. Clin Infect Dis. Feb. 15, 2001;32(4):647-9.
Navarro et al., Biomaterials in orthopaedics. J R Soc Interface. Oct. 6, 2008;5(27):1137-58.
Otto. *Staphylococcus epidermidis*—the ‘accidental’ pathogen. Nat Rev Microbiol. Aug. 2009;7(8):555-67.
Proctor et al., Persistent and relapsing infections associated with small-colony variants of *Staphylococcus aureus*. Clin Infect Dis. Jan. 1995;20(1):95-102.
Raper et al., The dictyostelids. Princeton, N.J.: Princeton University Press; 1984. TOC only. 4 pages.
Raper KB. Developmental patterns in simple slime molds. Growth. 1941;5:41-76.
Raper. *Dictyostelium discoideum*, a new species of slime mold from decaying forest leaves. J Agr Res. 1935;50:135-47.
Raper. Growth and development of Dictyostelium discoideum with bacterial associates. J Agr Res. 1937;55:289-316.
Rasmussen et al., Quorum-sensing inhibitors as anti-pathogenic drugs. Int J Med Microbiol. Apr. 2006;296(2-3):149-61.
Resch et al., Differential gene expression profiling of *Staphylococcus aureus* cultivated under biofilm and planktonic conditions. Appl Environ Microbiol. May 2005;71(5):2663-76.
Robson et al., Bacterial quantification of open wounds. Mil Med. Jan. 1969;134(1):19-24.
Rohde et al., Polysaccharide intercellular adhesin or protein factors in biofilm accumulation of *Staphylococcus epidermidis* and *Staphylococcus aureus* isolated from prosthetic hip and knee joint infections. Biomaterials. Mar. 2007;28(9):1711-20.
Rohde et al., Induction of *Staphylococcus epidermidis* biofilm formation via proteolytic processing of the accumulation-associated protein by staphylococcal and host proteases. Mol Microbiol. Mar. 2005;55(6):1883-95.
Rupp et al., Characterization of the importance of polysaccharide intercellular adhesin/hemagglutinin of *Staphylococcus epidermidis* in the pathogenesis of biomaterial-based infection in a mouse foreign body infection model. Infect Immun. May 1999;67(5):2627-32.
Rupp et al., Characterization of *Staphylococcus epidermidis* polysaccharide intercellular adhesin/hemagglutinin in the pathogenesis of intravascular catheter-associated infection in a rat model. Infect Immun. May 1999;67(5):2656-9.
Sanders et al., Multiple *Dictyostelid* Species Destroy Biofilms of Klebsiella oxytoca and Other Gram Negative Species. Protist. Jul. 2017;168(3):311-325.
Schaap et al., Molecular phylogeny and evolution of morphology in the social amoebas. Science. Oct. 27, 2006;314(5799):661-3.
SCHAAP. Evolutionary crossroads in developmental biology: Dictyostelium discoideum. Development. Feb. 2011;138(3):387-96.
Sutherland. The biofilm matrix—an immobilized but dynamic microbial environment. Trends Microbiol. May 2001;9(5):222-7.
Tielen et al., Extracellular enzymes affect biofilm formation of mucoid Pseudomonas aeruginosa. Microbiology (Reading). Jul. 2010;156(Pt 7):2239-2252.
Tomkin et al., Guidelines to Prevent Post-Processing Contamination from Listeria Monocytogenes. Dairy, Food Environ Sanit 1999; 19(8):551-62.
Walker et al., Enhanced Pseudomonas aeruginosa biofilm development mediated by human neutrophils. Infect Immun. Jun. 2005;73(6):3693-701.
Weitere et al., Grazing resistance of Pseudomonas aeruginosa biofilms depends on type of protective mechanism, developmental stage and protozoan feeding mode. Environ Microbiol. Oct. 2005;7(10):1593-601.
Welbourn et al., New Listeria Control Measures Under Consideration. Dairy, Food Environ Sanit 1999; 19:399-401.
Wong. Biofilms in food processing environments. J Dairy Sci. Oct. 1998;81(10):2765-70.
Yao et al., Genomewide analysis of gene expression in *Staphylococcus epidermidis* biofilms: insights into the pathophysiology of S. epidermidis biofilms and the role of phenol-soluble modulins in formation of biofilms. J Infect Dis. Jan. 15, 2005;191(2):289-98.
Zottola et al., Microbial biofilms in the food processing industry—should they be a concern? Int J Food Microbiol. Oct. 1994;23(2):125-48.

* cited by examiner

ANTI-BIOFILM AGENTS AND USES THEREOF

RELATED APPLICATIONS

This application claims priority to and the benefit of U.S. Provisional Patent Application No. 63/014,473 filed Apr. 23, 2020, which is incorporated herein by reference in its entirety for all purposes.

FIELD OF THE DISCLOSURE

The present disclosure relates to amoebae (e.g., Dictyostelids) and uses thereof. In particular, the present disclosure relates to anti-biofilm components of amoebae to target biofilms.

BACKGROUND OF THE DISCLOSURE

In the majority of cases, when humans develop a bacterial infection, the bacteria aggregate in complex associations called biofilms. Biofilms help protect the bacteria from assaults by the immune system and conventional antibiotics. New bioactive agents that disrupt the formation and/or maintenance of biofilms will facilitate healing, especially when patients are at risk for complications from chronic infections. Disrupting the biofilm may be sufficiently therapeutic on its own and/or the process may act to restore the antibiotic susceptibility of (formerly) biofilm-embedded bacteria.

Biofilm and chronic disease are interrelated, accounting for approximately 80% of bacterial infections (19, 20). In the U.S. alone, this leads to over 500,000 deaths annually. Biofilm-based infections are important for a wide range of ailments, including implanted medical devices, burn wounds, ear infections, and cystic fibrosis (21). The ability of biofilms to confer on bacteria antibiotic tolerance is what makes them a health threat. That tolerance can exceed 1,000 fold in comparison to planktonic counterparts (22).

Staphylococcal (*Staphylococcus aureus*, (MRSA) and *S. epidermidis* (Se)) infections are a particularly important clinical problem. Se is a common inhabitant of human skin capable of causing a variety of diseases including, infections of prosthetics, indwelling devices, and heart valves and it is often multi-drug resistant (Otto M. Nat Rev Microbiol. 2009; 7(8):555-67, Fey P D, Olson M E. Future Microbiol. 2010; 5(6):917-33.)

Se can readily be transferred to the skin of other individuals through contact or the constant sloughing of skin (dust). Se infections are typically chronic and highly recalcitrant to antibiotic treatment. Persister cells appear to be central to this recalcitrance (reviewed in Conlon B P. Bioessays. 2014; 36(10):991-6). Bone and joint degenerative and inflammatory problems affect millions of people worldwide, and account for half of all chronic diseases in people over 50 years of age in developed countries. The percentage of the population over 50 years of age affected by bone diseases is predicted to double by 2020 (Navarro M, et al., J R Soc Interface. 2008; 5(27):1137-58). Orthopedic procedures such as knee arthroplasty, hip replacement and spinal fusion, mitigate many of these conditions and improve patients' mobility and quality of life. However, orthopedic implants, bone fixation (for healing of a bone fracture) and joint replacement of irreversibly damaged articulation are highly susceptible to infection (Gustilo R B, et al., J Bone Joint Surg Am. 1990; 72(2):299-304.; Kessler B, et al., J Bone Joint Surg Am. 2012; 94(20):1871-6; Laffer R R, et al., Clin Microbiol Infect. 2006; 12(5):433-9; Murdoch, Clin Infect Dis. 2001; 32(4):647-9.)

Novel bioactive agents that disrupt the formation and/or maintenance of biofilms are needed to facilitate healing, especially when patients are at risk for complications from chronic infections. Disrupting the biofilm may be sufficiently therapeutic on its own and/or the process may act to restore the antibiotic susceptibility of (formerly) biofilm-embedded bacteria.

SUMMARY OF THE DISCLOSURE

The present disclosure relates to amoebae (e.g., Dictyostelids) and uses thereof. In particular, the present disclosure relates to anti-biofilm components of amoebae to target biofilms.

For example, in some embodiments, provided herein is a method of treating or preventing a biofilm accumulation, comprising: contacting a biofilm with a composition comprising one or more (e.g., two or more) amoebae components. In some embodiments, the amoebae components are biological molecules (e.g., proteins, small molecules, or metabolites) secreted by the amoebae. In some embodiments, the microorganism is bacteria (e.g., a pathogenic bacteria such as Se or MRSA, multi-drug resistant bacteria or persister cells of a bacteria) or a fungus. In some embodiments, the biofilm is in or on a subject. For example, in some embodiments, the biofilm is present in a wound, a mucus membrane (e.g., nostril, throat, ocular, rectum, vagina, etc.), a tissue or an organ of the subject. In some embodiments, the wound is at a temperature above the normal body temperature of the subject or is hypoxic. In some embodiments, the biofilm is in or on a plant (e.g., an agricultural or industrial plant) in or on materials (e.g., medical devices, industrial equipment, water processing or delivery systems, etc.). The present disclosure is not limited to a particular strain or species of amoebae. Examples include, but are not limited to, *Dictyostelium discoideum* (e.g., WS-28, WS-647, or AX3); *D. minutum* (e.g., Purdue 8a); *D. mucoroides* (e.g., Turkey 27, WS-20, WS-142, or WS-255); *D. mucoroides* complex (e.g., WS-309); *D. purpureum* (e.g., WS-321.5 or WS-321.7); *D. rosarium* (e.g., TGW-11); *D. sphaerocephalum* (e.g., FR-14); *Polysphondylium pallidum* (e.g., Salvador); *P. violaceum* (e.g., WS-371a) and unknown isolate Tu-4b. In some embodiments, the composition further comprises a non-amoebae anti-microbial agent, along with one or more carriers or other components. In some embodiments, the composition is a pharmaceutical composition. In some embodiments, the surface is a shower drain, water pipe, sewage pipe, food preparation surface, gas or oil pipeline, medical device, contact lens, or ship hull. In some embodiments, the biofilm is located on the surface at a facility selected from, for example, hospitals, laboratories, water treatment facilities, sewage treatment facilities, dental and/or medical offices, water distribution facilities, nuclear power plant, pulp or paper mill, air and/or water handling facility, pharmaceutical manufacturing facility, or dairy manufacturing facility.

Further embodiments provide a method of treating a subject infected with a biofilm, comprising: contacting a subject infected with a biofilm with a pharmaceutical composition comprising one or more amoebae components. In some embodiments, the subject is a human.

Yet other embodiments provide pharmaceutical composition, comprising: a) one or more amoebae components; and b) a pharmaceutically acceptable carrier.

Additional embodiments are described herein.

DEFINITIONS

Figure 1:
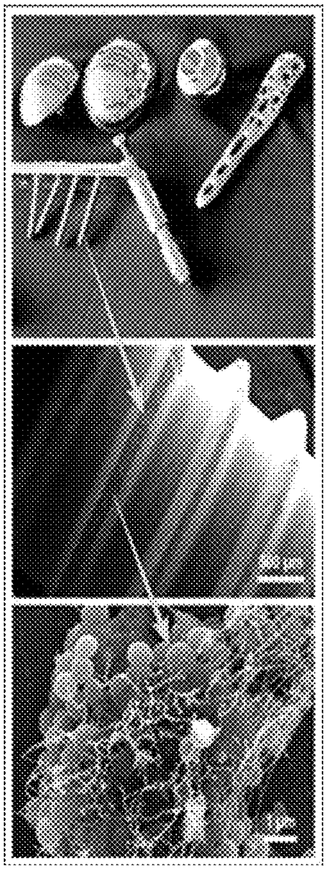
FIG. 1 shows biofilm-enmeshed Se cells grown on a bone screw. Top: Titanium orthopedic implants used in orthopedic surgeries. Middle and Bottom: Scanning electron microscopy images (40× and 14,000× mag.) of EPS-enmeshed Se.

To facilitate an understanding of the present disclosure, a number of terms and phrases are defined below.

The term "medical devices" includes any material or device that is used on, in, or through a subject's or patient's body, for example, in the course of medical treatment (e.g., for a disease or injury). Medical devices include, but are not limited to, such items as medical implants, wound care devices, drug delivery devices, birth control and body cavity and personal protection devices. Examples of medical implants include, but are not limited to, urinary catheters, intravascular catheters, dialysis shunts, wound drain tubes, skin sutures, vascular grafts, implantable meshes, intraocular devices, heart valves, and the like. Wound care devices include, but are not limited to, general wound dressings, biologic graft materials, tape closures and dressings, and surgical incision drapes. Drug delivery devices include, but are not limited to, needles, drug delivery skin patches, drug delivery mucosal patches and medical sponges. Body cavity and personal protection devices, include, but are not limited to, tampons, sponges, surgical and examination gloves, and toothbrushes. Birth control devices include, but are not limited to, intrauterine devices (IUDs), diaphragms, and condoms.

The term "therapeutic agent," as used herein, refers to compositions (e.g., comprising amoebae components) that decrease the infectivity, morbidity, or onset of mortality in a subject contacted by a pathogenic microorganism or that prevent infectivity, morbidity, or onset of mortality in a host contacted by a pathogenic microorganism. As used herein, therapeutic agents encompass agents used prophylactically, e.g., in the absence of a pathogen, in view of possible future exposure to a pathogen. Such agents may additionally comprise pharmaceutically acceptable compounds (e.g., adjutants, excipients, stabilizers, diluents, and the like). In some embodiments, the therapeutic agents of the present disclosure are administered in the form of topical compositions, injectable compositions, ingestible compositions, and the like. When the route is topical, the form may be, for example, a solution, cream, ointment, salve or spray.

As used herein, the term "pathogen" refers to a biological agent that causes a disease state (e.g., infection, cancer, etc.) in a host. "Pathogens" include, but are not limited to, bacteria, fungi, archaea, protozoans, mycoplasma, and other parasitic organisms.

As used herein, the term "microorganism" refers to any species or type of microorganism, including but not limited to, bacteria, archea, fungi, protozoans, mycoplasma, and parasitic organisms. The present disclosure contemplates that a number of microorganisms encompassed therein will also be pathogenic to a subject.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces*, and *Rickettsia*. All forms of bacteria are included within this definition including cocci, bacilli, spirochetes, spheroplasts, protoplasts, etc. Also included within this term are prokaryotic organisms that are gram negative or gram positive. "Gram negative" and "gram positive" refer to staining patterns with the Gram-staining process that is well known in the art. (See e.g., Finegold and Martin, Diagnostic Microbiology, 6th Ed., CV Mosby St. Louis, pp. 13-15 [1982]). "Gram positive bacteria" are bacteria that retain the primary dye used in the Gram stain, causing the stained cells to appear dark blue to purple under the microscope. "Gram negative bacteria" do not retain the primary dye used in the Gram stain, but are stained by the counterstain. Thus, gram negative bacteria appear red. In some embodiments, the bacteria are those capable of causing disease (pathogens) and those that cause production of a toxic product, tissue degradation or spoilage.

As used herein, the term "fungi" is used in reference to eukaryotic organisms such as the molds and yeasts, including dimorphic fungi.

As used herein the term "biofilm" refers to an aggregation of microorganisms (e.g., bacteria) surrounded by an extracellular matrix or slime adherent on a surface in vivo or ex vivo, wherein the microorganisms adopt altered metabolic states. Planktonic cells are innate elements of both the biofilm formation and erosion processes (Costerton J W, Stewart P S, Greenberg E P. Bacterial biofilms: a common cause of persistent infections. Science. 1999; 284(5418): 1318-22).

As used herein, the term "non-human animals" refers to all non-human animals including, but are not limited to, vertebrates such as rodents, non-human primates, ovines, bovines, lagomorphs, porcines, caprines, equines, canines, felines, ayes, etc.

As used herein, the term "subject" refers to organisms to be treated by the methods of embodiments of the present disclosure. Such organisms preferably include, but are not limited to, mammals (e.g., murines, simians, equines, bovines, porcines, canines, felines, and the like), and most preferably includes humans. In the context of the disclosure, the term "subject" generally refers to an individual who will receive or who has received treatment (e.g., administration of a amoebae of the present disclosure and optionally one or more other agents) for a condition characterized by infection by a microorganism or risk of infection by a microorganism.

The term "diagnosed," as used herein, refers to the recognition of a disease by its signs and symptoms (e.g., resistance to conventional therapies), or genetic analysis, pathological analysis, histological analysis, diagnostic assay (e.g., for microorganism infection) and the like.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the term "host cell" refers to any eukaryotic or prokaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "genome" refers to the genetic material (e.g., chromosomes) of an organism or a host cell.

As used herein, the term "effective amount" refers to the amount of a therapeutic agent (e.g., an amoebae component) sufficient to effect beneficial or desired results. An effective amount can be administered in one or more administrations, applications or dosages and is not intended to be limited to a particular formulation or administration route.

As used herein, the term "co-administration" refers to the administration of at least two agent(s) (e.g., an amoeba component) or therapies to a subject. In some embodiments, the co-administration of two or more agents/therapies is concurrent. In some embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "toxic" refers to any detrimental or harmful effects on a cell or tissue as compared to the same cell or tissue prior to the administration of the toxicant.

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, PA [1975]).

The term "sample" as used herein is used in its broadest sense. A sample may comprise a cell, tissue, or fluids, nucleic acids or polypeptides isolated from a cell (e.g., a microorganism), and the like.

As used herein, the terms "purified" or "to purify" refer, to the removal of undesired components from a sample. As used herein, the term "substantially purified" refers to molecules that are at least 60% free, preferably 75% free, and most preferably 90%, or more, free from other components with which they usually associated.

As used herein, the term "modulate" refers to the activity of a compound (e.g., an amoebae component) to affect (e.g., to kill or prevent the growth of) a microorganism.

The term "test compound" refers to any chemical entity, pharmaceutical, drug, and the like, that can be used to treat or prevent a disease, illness, sickness, or disorder of bodily function, or otherwise alter the physiological or cellular status of a sample (e.g., infection by a microorganism). Test compounds comprise both known and potential therapeutic compounds. A test compound can be determined to be therapeutic by using the screening methods of the present disclosure. A "known therapeutic compound" refers to a therapeutic compound that has been shown (e.g., through animal trials or prior experience with administration to humans) to be effective in such treatment or prevention. In some embodiments, "test compounds" are agents that treat or prevent infection by a microorganism.

DETAILED DESCRIPTION OF THE DISCLOSURE

The present disclosure relates to amoebae (e.g., Dictyostelids) and uses thereof. In particular, the present disclosure relates to anti-biofilm components of amoebae to target biofilms.

Figure 2:
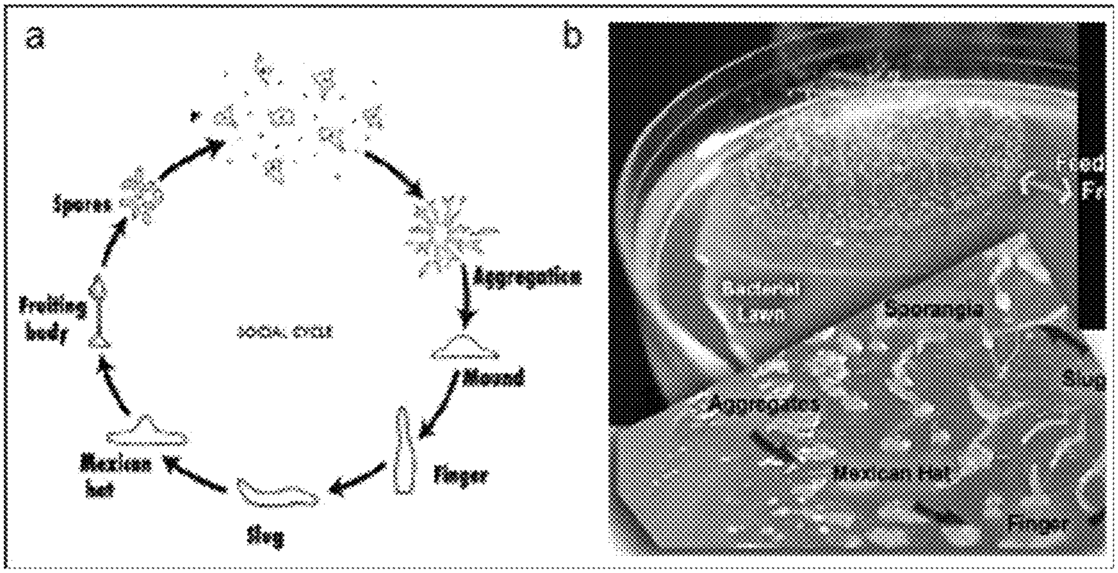
FIG. 2 shows multicellular development of Dictyostelids schematic (a) and in vivo (b). Dicty emerge from spores as motile phagocytic amoebae and feed on bacterial lawns. Upon starvation, slugs form, migrate, and produce fruiting bodies.
Figure 3:
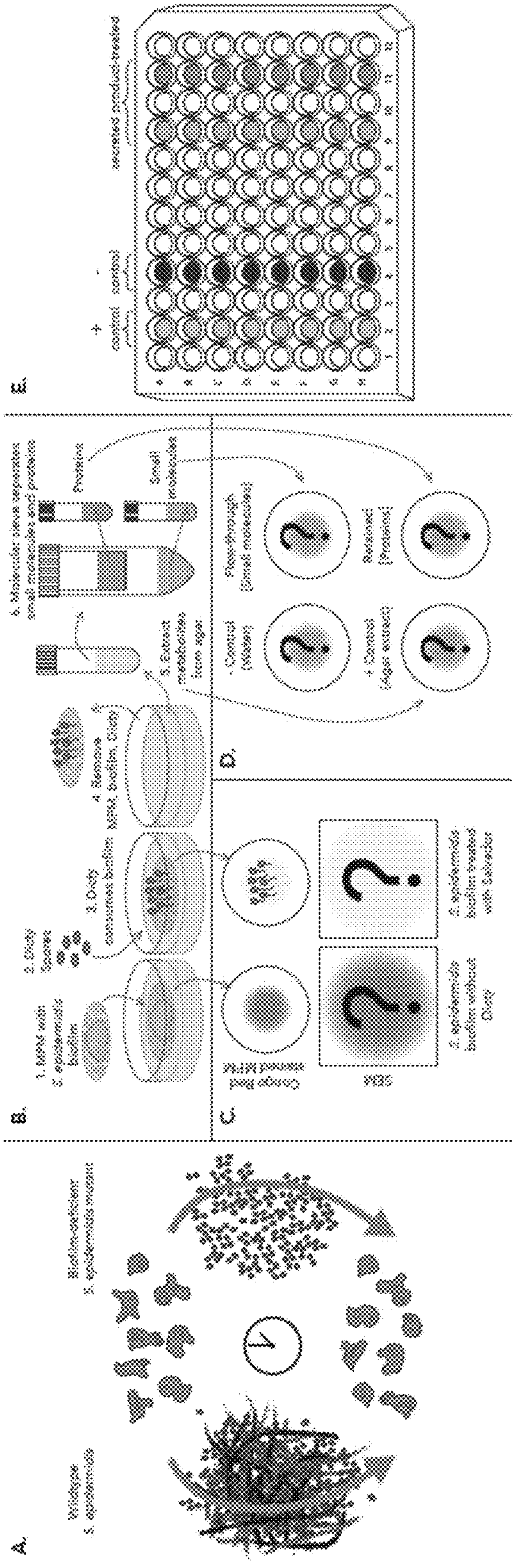
FIG. 3 shows an exemplary experimental approach aimed at discovering secreted products by Dictyostelids grazing upon bacterial prey. Schematic of method for testing biofilm-degrading component production by Dicty with preliminary results from PpS. (A) experimental setup for collection of secreted products. (B) Images of the MPMs are taken using dissecting (top) and scaning electron microscopy, SEM (bottom) micrographs. (C) Application of whole metabolite extract as well as the large-molecule fraction are used to monitor biofilm destruction activity. D) Application of whole secreted products are used to monitor biofilm destruction activity using microplate method.

Dicty (39, 40), are members of a single clade within the supergroup of Amoebozoa (10, 15, 41, 42). Nearly all known species (circa 100) of Dicty have been subdivided into five major groups based on phylogenetic analysis of their 18S ribosomal RNA sequences (15). When presented with bacterial prey, dictyostelids feed, grow and divide in the form of solitary phagocyte. Without bacteria, starvation leads to a transition from the solitary form to a multicellular assemblage comprised of non-feeding cells, which undergo complex development culminating in the production of spore-laden son (17, 40, 43-45) (FIG. 2) General strategies employed while studying antibiofilm properties of Dictyostelids themselves and the products they secrete are outlined in FIG. 3.

In many ecosystems, biofilm-enmeshed (rather than planktonic) bacteria predominate both in metabolic activity and number. Biofilms provide protection from a wide range of abiotic and biotic challenges including phagocytic predation by Dicty (Matz C, Kjelleberg S. TrendsMicrobiol. 2005; 13(7):302-7). Indeed, the feeding rates of phagocytic predators on biofilms are considerably lower compared to planktonic bacteria (Matz, 2005; Weitere, 2005). Some biofilms provide a protective matrix that enables bacteria to survive or even kill grazing protozoans while their planktonic counterparts are eliminated (Matz C, Kjelleberg S. TrendsMicrobiol. 2005; 13(7):302-7). Biofilm-specific traits that might effectively limit assaults by phagocytic predators have perhaps forced some predators to evolve chemical/mechanical counter-strategies.

It was determined that Dicty strains tested unequally destroy biofilms of human and plant pathogens (Filutowicz and Borys: U.S. Pat. Nos. 8,551,471 and 8,715,641 and Sanders D., Borys K, et al., Protist. 2017; 168(3):311-25). Taken together, the qualitative and quantitative data indicate that Dicty have preferences in bacterial prey, which affect their efficiency of feeding on bacterial biofilms. Some Dicty feed equally well on phytopathogen *Ervinia amylowora* regardless of whether this bacterium produces or does not produce EPS (Sanders D., Borys K, et al., Protist. 2017; 168(3):311-25).

Most bioactive compounds used to fight bacterial infections are natural products (NPs) produced by other bacteria and fungi, primarily a circumscribed group that live in the soil. The microbes use chemicals as a means of interacting with their environments and one another, and many of the compounds are produced by polyketide synthase (PKS) enzymes. In addition to the soil microbes mentioned, Dictyostelids occupy similar micro-environments and rely on similar strategies for survival. For example, four sequenced and annotated Dictyostelid genomes exhibit the largest repository of PKS enzymes of all known genomes. This is significant because, although the rate of discovery of new bioactive NPs from traditional sources is diminishing, amoebae have not been examined in this regard. It has been shown that Dictyostelids prey on biofilm-enmeshed bacteria. Experiments conducted during the course of development of the embodiments of the present disclosure demonstrated that Dictyostelids secrete compounds that influence patterns of bacterial growth.

Compounds that can prevent biofilm formation or disrupt the biofilm matrix are of great clinical interest. The extracellular polymeric substances (EPS), which may represent 85% of total biofilm biomass, is an attractive target for anti-biofilm agents as it is composed of polysaccharides, proteins, nucleic acids and lipids (29-33). Correspondingly, the degradation of the matrices, is caused by extracellular enzymes such as glycosidases, proteases, and deoxyribonucleases (31, 34). Therefore, it indicates that multiple combined activities may be most effective in perturbing biofilms. In addition to EPS, many other factors have been implicated as drivers of reversible biofilm-mediated tolerance to antibiotics, including slower growth kinetics, higher cell densities, reduced antibiotic diffusion, enhanced expression of drug efflux pumps, and the formation of dormant persister cells (35). The relevance of using antibiofilm compounds is based on the restoration of effectiveness of many antibiotics by facilitating their penetration through compromised biofilm structure. Moreover, a degradation of the biofilm matrix may render bacteria reachable by the cells of the immune system (36-38).

Therefore, it is contemplated that multiple combined activities may be most effective in breaking down EPS (Mah T F, O'Toole G A. TrendsMicrobiol. 2001; 9(1):34-9); Walker T S, et al., Infect Immun. 2005; 73(6):3693-701; Chiang W C, et al., Antimicrob Agents Chemother. 2013; 57(5):2352-61; Sutherland I W. Trends Microbiol. 2001; 9(5):222-7). See also, for extensive reviews Otto M. Nat. Rev. Microbiol. 2009; 7(8):555-67; Fey P D, Olson M E. Future Microbiol. 2010; 5(6):917-33).

In some embodiments, the hydrolytic enzymes and secondary metabolites or other factors that these organisms produce assist in breaking EPS to liberate cells prior to phagocytosis. In fact, experiments described herein with thermophilic strain of *Polysphondillum pallidum* Salvador (*P. pallidum* Salvador, PpS) grazing upon biofilm-enmeshed cells of *Staphylococcus epidermidis* (*S. epidermidis*, Se) support that Dicty phagocytose cells and concomitantly destroy EPS. The experiments have firmly established the efficacy of PpS against Se biofilms in vitro, determined that biofilm breakdown is facilitated by compound/s secreted during PpS feeding on Se bacteria. An evaluation of the molecular weight of the bioactive compound/s was determined by testing secreted samples after filtration (Millipore MW cutoff, $3\times10^{3}$). The data show that large molecules (e.g., proteins), facilitate biofilm breakdown. In view of an exceptional abundance and diversity of the secreted proteome by developing Dicty cells (e.g., 349 proteins) (Bakthavatsalam D, Gomer R H. Proteomics. 2010; 10(13): 2556-9) it is contemplated that the secreted proteins break down the components of Se EPS. *S. epidermis* cells are encased in an EPS matrix composed of proteins, polysaccharides, extracellular DNA (eDNA) and presumably host factors (see for extensive reviews Otto M. Nat. Rev. Microbiol. 2009; 7(8):555-67; Fey P D, Olson M E. Future Microbiol. 2010; 5(6):917-33). Correspondingly, the degradation of the matrices is caused by extracellular enzymes such as glycosidases, proteases, and deoxyribonucleases (Branda S S, et al., Mol Microbiol. 2006; 59(4):1229-38; Boles B R, Horswill A R. Trends in Microbiology. 2011; 19(9):449-55).

Accordingly, provided herein are amoebae components for use in treating and preventing biofilm formation, alone and in combination with additional agents.

I. Amoebae Components

As described above, embodiments of the present disclosure provide compositions and methods for treating and preventing biofilm formation or killing or preventing growth of microorganisms with amoebae components. The present disclosure is not limited to particular amoebae components. Examples include, but are not limited to, secreted components and cellular components (e.g., extracts). In some embodiments, the amoebae component is a protein, nucleic acid, metabolite, small molecule, enzyme or other component or combinations thereof. Exemplary components can be identified, for example, using the methods in examples 1 to 4 below. Anti-biofilm components may be prepared and isolated as described in the examples. Use of these components provides advantages in setting where treatment of biofilms with live organism amoebae is not practical or otherwise desired.

Examples of amoebae suitable for use in embodiments of the present disclosure include, but are not limited to, amoebae of the phylum Mycetozoa, which include but are not limited to: *Dictyostelium: D. laterosorum, D. tenue, D. potamoides, D. minutum, D. gracile, D. lavandulum, D. vinaceo-fuscum, D. rhizopodium, D. coeruleo-stipes, D. lacteum, D. polycephalum, D. polycarpum, D. polycarpum, D. menorah, D. caveatum, D. gloeosporum, D. oculare, D. antarcticum, D. fasciculatum, D. delicatum, D. fasciculatum, D. aureo-stipes* var. *helveticum, D. granulophorum, D. medusoides, D. mexicanum, D. bifurcatum, D. stellatum, D. microsporum, D. parvisporum, D. exiguum* TNS-C-199, *D. mucoroides, D. sphaerocephalum, D. rosarium, D. clavatum, D. longosporum, D. macrocephalum, D. discoideum, D. discoideum* AX4, *D. intermedium, D. firmibasis, D. brunneum, D. giganteum, D. robustum, D. multi-stipes, Dermamoeba algensis, D. brefeldianum, D. mucoroides, D. capitatum, D. pseudobrefeldianum, D. aureocephalum, D. aureum, D. septentrionalis, D. septentrionalis, D. implicatum, D. medium, D. sphaerocephalum, D. rosarium, D. clavatum, D. longosporum, D. purpureum, D. macrocephalum, D. citrinum, D. dimigraformum, D. firmibasis, D. brunneum, D. giganteum, D. monochasioides, Thecamoeba similis* and *Polysphondylium: P. violaceum, P. filamentosum, P. luridum, P. pallidum, P. equisetoides, P. nandutensis* YA, *P. colligatum, P. tikaliensis, P. anisocaule, P. pseudocandidum, P. tenuissimum, P. pallidum, P. asymmetricum, P. filamentosum, P. tenuissimum, P. candidum. Acytostelium; A. ellipticum, A. anastomosans, A. longisorophorum, A. leptosomum, A. digitatum, A. serpentarium, A. subglobosum, A. irregularosporum. Acraside; A. granulate, A. rosea; Copromyxa: C. protea, C. arborescens, C. filamentosa*, and *C. corralloides; Guttulina* (Pocheina) *G. rosea; Guttulinopsis G. vulgaris, G. clavata, G. stipitata, G. nivea* (See e.g., Schaap, et al. 2006 Molecular Phylogeny and Evolution of Morphology in the Social Amoebas, Science 27 Oct. 2006: 661-663; Raper K B. 1984. The Dictyostelids. Princeton University Press. Princeton NJ; each of which is herein incorporated by reference in its entirety).

Examples of specific isolates include, but are not limited to, *Dictyostelium discoideum* (WS-28 and WS-647 and AX3); *D. minutum* (Purdue 8a); *D. mucoroides* (Turkey 27, WS-20, WS-142, WS-255); *D. mucoroides* complex (WS-309); *D. purpureum* (WS-321.5 and WS-321.7); *D. rosarium* (TGW-11); *D. sphaerocephalum* (FR-14); *Polysphondylium pallidum* (Salvador); *P. violaceum* (WS-371a) and unknown isolate Tu-4b.

The amoebae described herein can be obtained, for example, from ATCC and the Bacteriology Department at the University of Wisconsin Madison, which has maintained a large collection of amoebae since the 1930s and keeps detailed records on all strains and isolates.

In some embodiments, the present disclosure provides kits and/or compositions comprising amoebae components. In some embodiments, compositions comprise additional components (e.g., buffers, preservatives, stabilizers, etc.). In some embodiments, the composition comprises a secreted component. In some embodiments, the composition comprises an extract. In some embodiments, the compositions comprise a fraction of a secreted component or extract (e.g., partially or completely purified amoebae component).

In some embodiments, the present disclosure also provides preparations for treating or preventing biofilm formation in clinical, agricultural, research and industrial applications. In certain clinical applications, these preparations comprise one of the aforementioned amoebae components, formulated for the appropriate use. In some embodiments amoebae components are incorporated into bandages, dressings, or other wound coverings. In addition, in some embodiments, amoebae components are incorporated into salves, ointments, or other topical applications.

In some embodiments, amoebae components are delivered by pharmaceutically acceptable carrier, that refers to any of the standard pharmaceutical carriers including, but not limited to, saline solution, water, emulsions (e.g., such as an oil/water or water/oil emulsions), and various types of wetting agents, any and all solvents, dispersion media, coatings, sodium lauryl sulfate, isotonic and absorption delaying agents, disintrigrants (e.g., potato starch or sodium starch glycolate), and the like. The compositions also can include stabilizers and preservatives. For example, of carriers, stabilizers, and adjuvants. (See e.g., Martin, Remington's Pharmaceutical Sciences, 15th Ed., Mack Publ. Co., Easton, Pa. (1975), incorporated herein by reference). Moreover, in certain embodiments, the compositions of the present disclosure may be inoculated for horticultural or agricultural use. Such formulations include dips, sprays, seed dressings, stem injections, sprays, and mists.

The pharmaceutical compositions of the present disclosure may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intra-arterial, subcutaneous, intraperitoneal or intramuscular injection or infusion; or intracranial, e.g., intrathecal or intraventricular, administration.

Pharmaceutical compositions and formulations for topical administration (e.g., to tissues, wounds, organs, etc) may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present disclosure include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present disclosure, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present disclosure may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present disclosure, such as dyes, flavoring agents, preservatives, antioxidants, opacifiers, thickening agents and stabilizers. However, such materials, when added, should not unduly interfere with the biological activities of the components of the compositions of the present disclosure. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the active agents of the formulation.

Dosing is dependent on severity and responsiveness of the disease state or condition to be treated, with the course of treatment lasting from several days to several months, or until a cure is effected or a diminution of the disease state is achieved. In some embodiments, treatment is administered in one or more courses, where each course comprises one or more doses per day for several days (e.g., 1, 2, 3, 4, 5, 6) or weeks (e.g., 1, 2, or 3 weeks, etc.). In some embodiments, courses of treatment are administered sequentially (e.g., without a break between courses), while in other embodiments, a break of 1 or more days, weeks, or months is provided between courses. In some embodiments, treatment is provided on an ongoing or maintenance basis (e.g., multiple courses provided with or without breaks for an indefinite time period). Optimal dosing schedules can be calculated from measurements of drug accumulation in the body of the patient. The administering physician can readily determine optimum dosages, dosing methodologies and repetition rates.

II. Uses

Embodiments of the present disclosure provide compositions and methods for the therapeutic, clinical, research, agricultural and industrial use of amoebae. Exemplary applications are discussed herein.

In some embodiments, amoebae components are used in the treatment of subjects (e.g., humans or non-human animals) infected with a microorganism (e.g., pathogenic bacteria in a biofilm or other growth stage). In some embodiments, amoebae components are used on infected skin wounds.

Chronically infected wounds present a significant burden to the healthcare system both in terms of individual and societal costs. Two important factors hamper successful treatment of these wounds: The lack of unified criteria for employing different treatments and the lack of proven treatment regimens. Against this backdrop of variability, the idea that a critical microbial load is a principal determining factor in wound healing has fared remarkably well. Numerous studies have demonstrated that the microbial load is a reliable predictive indicator of successful treatment outcomes (Bendy et al., (1964) Antimicrob. Agents Chemother (Bethesda) 10: 147-55; Bergstrom et al., (1994) Treatment of pressure ulcers. Clinical practice guideline, No. 15; Bowler P G. (2002) Wound pathophysiology, infection and therapeutic options. Ann Med 34(6): 419-27; Krizek T J, Robson M C. (1975) Am J Surg 130(5): 579-84; Robson M C, Heggers J P. (1969) Mil Med 134(1): 19-24; Daltrey et al., (1981) J Clin Pathol 34(7): 701-5. PMCID: PMC493797; Dow G. (2001) Infection in chronic wounds. Chronic Wound Care: A Clinical Source Book for Healthcare Professionals: 343-56). These studies all discuss that $10^5$ organisms per gram of tissue is the breakpoint beyond which wounds become non-healing. The best current practices aim at keeping the localized concentration of bacteria in wounds well below this threshold, typically through the administration of systemic antibiotics and surgical debridement (Bowler P G., 2002, Ann Med 34(6): 419-27). The treatment of chronic infections of the skin often is a challenge to clinicians. Infected, burns, surgical wounds, and diabetic lesions can be refractory to current treatment regimes causing them to persist as open sores. The most common underlying reasons for this type of pathology are: antibiotic failure due to high bacterial loads, infection with multiple antibiotic-resistant pathogens, or the formation of antibiotic-tolerent biofilms. Clinicians are demanding new and more effective therapies.

Recently, owing to the frequency of therapeutic failures, there has been growing interest in the development and use of topical antimicrobial agents. Biotherapeutics for disease can be found in bacteriophage, bacterial interference, and leech and maggot therapies. For instance, bacteriophage therapy, as an alternative or adjunct to chemical antibiotics, has been advanced in Eastern Europe. Presently, this strategy is receiving renewed attention in Great Britain and in the United States. Phage therapy uses mixtures of lytic viruses to kill pathogenic bacteria (Mann N H, 2008. Res Microbiol. 159:400-405). A second strategy, bacterial interference, uses live benign bacteria to displace pathogenic organisms by competition for space. Several examples of this technology are in the research stage (Huovinen P. 2001. BMJ. 323:353-354, and U.S. Pat. No. 6,991,786). The US Food and Drug Administration has approved both leeches and maggots as Class II medical devices. Leeches are used in the treatment of venous congestion (Zhang X, et al. 2008. J Hand Surg Am. 33:1597-601), and maggots are used to disinfect and debride wounds (Hunter S, et al. 2009, Adv Skin Wound Care. 22:25-27).

The use of biologics is much broader than those examples mentioned above. For example, preparations of the prokaryote *Lactobacillus acidophilus* for use in human therapies is known (see, e.g., U.S. Pat. Nos. 5,032,399 and 5,733,568). In addition, pharmaceutical preparations of *Lactobacillus acidophilus* are known (See e.g., U.S. Pat. No. 4,314,995). Additional applications of biologics in human therapy are described in U.S. Pat. No. 5,607,672 (Using recombinant *Streptococcus mutans* in the mouth to prevent tooth decay); U.S. Pat. No. 6,447,784 15 (Genetically modified tumor-targeted bacteria (*Salmonella*) with reduced virulence); U.S. Pat. No. 6,723,323 (*Vibrio cholerae* vaccine candidates and method of their constructing); U.S. Pat. No. 6,682,729 (A method for introducing and expressing genes in animal cells is disclosed comprising infecting the animal cells with live invasive bacteria); and U.S. Pat. No. 4,888,170 (relating to a vaccine for the immunization of a vertebrate, comprising: an avirulent derivative of a 20 pathogenic microbe).

In some embodiments, amoebae components are utilized in the treatment of microbial infections (e.g., biofilms) in mucus membranes (e.g., nostrils, throat, rectum, vagina, etc.), tissues or organs (e.g., urinary tract, etc) or bodily fluids (e.g., blood).

In some embodiments, amoebae components are utilized in the treatment of infection by drug or multi-drug resistant bacteria (e.g., methycillin resistant Staph *aureus* (MRSA) or MDR (multi-drug resistant) *Acinetobacter baumannii*) or dormant persister cells (e.g., in biofilms).

Dormant persister cells are tolerant to antibiotics and are largely responsible for recalcitrance of chronic infections. Chronic infections are often caused by pathogens that are susceptible to antibiotics, but the disease may be difficult or even impossible to eradicate with antimicrobial therapy. For many pathogens, including *S. aureus*, a highly significant factor of virulence steams from the fact that in addition to fast-growing cells these pathogens produces small numbers of dormant persister cells whose function is survival in adverse circumstances. Persisters are not mutants, but phenotypic variants of the wild type, and are tolerant to killing by antibiotics. The dormancy protection from antibiotics is mechanistically distinct from genetically determined MRSA. Antimicrobial therapy, however, selects for high persistence mutants, or Small Colony Variants (SCVs). SCVs have been found for many genera of bacteria, but they have been most extensively studied for staphylococci. (Proctor et al., Clin. Infect. Dis. 20, 95-102 (1995). *S. aureus* SCVs can also cause more aggressive infections in both humans and animals. The high rate of selection by aminoglycosides indicates that SCVs are part of the normal life cycle of staphylococci. (Massey et al., Curr. Biol. 11, 1810-1814 (2001). Massey, R. C. & Peacock, S. J. Curr. Biol. 12, R686-R687 (2002).

In some other embodiments, the present methods and compositions are directed to specifically controlling (e.g., therapeutic treatments or prophylactic measures) diseases caused by the following pathogens: *Bartonella henselae, Borrelia burgdorferi, Campylobacter jejuni, Campylobacter fetus, Chlamydia trachomatis, Chlamydia pneumoniae, Chylamydia psittaci, Simkania negevensis, Escherichia coli* (e.g., 0157:H7 and K88), *Ehrlichia chafeensis, Clostridium botulinum, Clostridium perfringens, Clostridium tetani, Enterococcus faecalis, Haemophilius influenzae, Haemophilius ducreyi, Coccidioides immitis, Bordetella pertussis, Coxiella burnetii, Ureaplasma urealyticum, Mycoplasma genitalium, Trichomatis vaginalis, Helicobacter pylori, Helicobacter hepaticus, Legionella pneumophila, Mycobacterium tuberculosis, Mycobacterium bovis, Mycobacterium africanum, Mycobacterium leprae, Mycobacterium asiaticum, Mycobacterium avium, Mycobacterium celatum, Mycobacterium celonae, Mycobacterium fortuitum, Mycobacterium genavense, Mycobacterium haemophilum, Mycobacterium intracellulare, Mycobacterium kansasii, Mycobacterium malmoense, Mycobacterium marinum, Mycobacterium scrofulaceum, Mycobacterium simiae, Mycobacterium szulgai, Mycobacterium ulcerans, Mycobacterium xenopi, Corynebacterium diptheriae, Rhodococcus equi, Rickettsia aeschlimannii, Rickettsia africae, Rickettsia conorii, Arcanobacterium haemolyticum, Bacillus anthracis, Bacillus cereus, Lysteria monocytogenes, Yersinia pestis, Yersinia enterocolitica, Shigella dysenteriae, Neisseria meningitides, Neisseria gonorrhoeae, Streptococcus bovis, Streptococcus hemolyticus, Streptococcus mutans, Streptococcus pyogenes, Streptococcus pneumoniae, Staphylococcus aureus, Staphylococcus epidermidis, Staphylococcus pneumoniae, Staphylococcus saprophyticus, Vibrio cholerae, Vibrio parahaemolyticus, Salmonella typhi, Salmonella paratyphi, Salmonella enteritidis* and *Treponema pallidum.*

In some embodiments, compositions of the present disclosure are used to treat surfaces. Surfaces that can be treated by the methods and compositions of the present disclosure include but are not limited to, surfaces of a medical device (e.g., a catheter, implants, stents, etc.), a wound care device, a body cavity device, a human body, an animal body, a food preparation surface, an industrial surface, a personal protection device, a birth control device, and a drug delivery device. Surfaces include but are not limited to silicon, plastic, glass, polymer, ceramic, skin, tissue, nitrocellulose, hydrogel, paper, polypropylene, cloth, cotton, wool, wood, brick, leather, vinyl, polystyrene, nylon, polyacrylamide, optical fiber, natural fibers, nylon, metal, rubber, soil and composites thereof. In some embodiments, the treating destroys growing, nongrowing, or dormant microbial pathogens (e.g., in a biofilm).

In some embodiments, amoebae components are used in the treatment of microbial infections of agricultural and industrial plants.

As described above, in some embodiments, the methods and compositions of the present disclosure target bacteria present as a biofilm. Biofilms can be broadly defined as microbial cells attached to a surface, and which are embedded in a matrix of extracellular polymeric substances produced by the microorganisms. Biofilms are known to occur in many environments and frequently lead to a wide diversity of undesirable effects. For example, biofilms cause fouling of industrial equipment such as heat exchangers, pipelines, and ship hulls, resulting in reduced heat transfer, energy loss, increased fluid frictional resistance, and accelerated corrosion. Biofilm accumulation on teeth and gums, urinary and intestinal tracts, and implanted medical devices such as catheters and prostheses frequently lead to infections (Characklis W G. Biofilm processes. In: Characklis W G and Marshall K C eds. New York: John Wiley & Sons, 1990: 195-231; Costerton et al., Annu Rev Microbiol 1995; 49:711-45).

Biofilm formation is a serious concern in the food processing industry because of the potential for contamination of food products, leading to decreased food product quality and safety (Kumar C G and Anand S K, Int J Food Microbiol 1998; 42:9-27; Wong, J Dairy Sci 1998; 81:2765-70; Zottola and Sasahara, Int J Food Microbiol 1994; 23:125-48). The surfaces of equipment used for food handling or processing are recognized as major sources of microbial contamination. (Dunsmore et al., J Food Prot 1981; 44:220-40; Flint et al., Biofouling 1997; 11:81-97; Grau, In: Smulders F J M ed. Amsterdam: Elsevier, 1987:221-234; Thomas et al., In: Smulders F J M ed. Amsterdam: Elsevier, 1987:163-180). Biofilm bacteria are generally hardier than their planktonic (free-living) counterparts, and exhibit increased tolerance to antimicrobial agents such as antibiotics and disinfectants. It has been shown that even with routine cleaning and sanitizing procedures consistent with good manufacturing practices, bacteria can remain on equipment, food and non-food contact surfaces and can develop into biofilms. In addition, *Listeria monocytogenes* attached to surfaces such as stainless steel and rubber, materials commonly used in food processing environments, can survive for prolonged periods (Helke and Wong, J Food Prot 1994; 57:963-8). This would partially explain their ability to persist in the processing plant. Common sources of *L. monocytogenes* in processing facilities include equipment, conveyors, product contact surfaces, hand tools, cleaning utensils, floors, drains, walls, and condensate (Tomkin et al., Dairy, Food Environ Sanit 1999; 19:551-62; Welbourn and Williams, Dairy, Food Environ Sanit 1999; 19:399-401).

Bacterial growth and survival in the environment as well as in association with human hosts are constrained by the action of phagocytic eukaryotic cells. Phagocytic predation on bacteria by host immune cells shares a number of cellular mechanisms with free-living protozoa. In and outside the human host, bacteria growing in biofilms appear to be less vulnerable to phagocytic predators than planktonic cells. Widespread resistance against predators is mediated by the interplay of biofilm-specific traits such as substratum adherence, exopolymer production, cellular cooperation, inhibitor secretion, and phenotypic variation.

An important mortality factor in the control of bacterial populations is the uptake and killing of bacteria by phagocytic eukaryotic cells (See e.g., Matz, Biofilms and Predations, 194-213 in The Biofilm Mode of Life: Mechanisms and Adaptations, Horizon Bioscience Editor: Staffan Kjelleberg and Michael Givskov, June 2007; herein incorporated by reference in its entirety). Accordingly, embodiments of the present disclosure provide compositions and methods for the use of amoebae components in the killing of bacteria present in biofilms.

In some embodiments, compositions for use in killing microorganisms utilize two or more amoebae components. In some embodiments, one or more amoebae components are administered in combination with known anti-microbial agents. There are an enormous amount of antimicrobial agents currently available for use in treating bacterial and fungal. For a comprehensive treatise on the general classes of such drugs and their mechanisms of action, the skilled artisan is referred to Goodman & Gilman's "The Pharmacological Basis of Therapeutics" Eds. Hardman et al., 9th Edition, Pub. McGraw Hill, chapters 43 through 50, 1996, (herein incorporated by reference in its entirety). Generally, these agents include agents that inhibit cell wall synthesis (e.g., penicillins, cephalosporins, cycloserine, vancomycin, bacitracin); and the imidazole antifungal agents (e.g., miconazole, ketoconazole and clotrimazole); agents that act directly to disrupt the cell membrane of the microorganism (e.g., detergents such as polmyxin and colistimethate and the antifungals nystatin and amphotericin B); agents that affect the ribosomal subunits to inhibit protein synthesis (e.g., chloramphenicol, the tetracyclines, erthromycin and clindamycin); agents that alter protein synthesis and lead to cell death (e.g., aminoglycosides); agents that affect nucleic acid metabolism (e.g., the rifamycins and the quinolones); and antimetabolites (e.g., trimethoprim and sulfonamides). Various combinations of antimicrobials may be employed.

EXPERIMENTAL

The following examples are provided in order to demonstrate and further illustrate certain preferred embodiments and aspects of the present disclosure and are not to be construed as limiting the scope thereof.

Example 1

Several other reasons, in addition to its clinical relevance (See Background) led to the choice of Se as the representative pathogen for this example: 1) Se was considered an atypical prey for Dicty, which consume predominantly the soil bacteria (Raper K B, Rahn A W. The dictyostelids. Princeton, N.J.: Princeton University Press; 1984. x, 453 p. p; Horn E. Ecology. 1971; 52(3):475-84. 2) The importance of biofilm in the virulence of Se was demonstrated in two animal models of device-associated infections (Li H, et al., Infect Immun; Rupp M E, et al., Infect Immun. 1999; 67(5):2627-32. 2005; 73(5):3188-91.; Rupp M E, et al., Infect Immun. 1999; 67(5):2656-9; Rupp M E, et al., Infect Immun. 1999; 67(5):2627-32). 3) Biofilm accumulation proteins in Se include Aap, which is a fibrillary EPS protein extruded from the cell in localized tufts (see FIG. 1, bottom panel) (Rohde H, et al., Mol Microbiol. 2005; 55(6):1883-95; Banner M A, et al., J Bacteriol. 2007; 189(7):2793-804), and found in approximately 90% of Se isolates, explaining the remarkable resistance of Se biofilm to mechanical forces or sonication and the sensitivity of Se biofilm to proteases (Rohde H, et al., Biomaterials. 2007:28 (9).1711-20). 4) The availability of microarray data that have demonstrated that Se growing in a biofilm state have unique transcriptional responses compared with cells growing planktonically (Beenken K E, et al., J Bacteriol. 2004; 186(14):4665-84; Yao Y, et al., J Infect Dis. 2005; 191(2):289-98; Resch A, et al., Appl Environ Microbiol. 2005; 71(5):2663-76.)

Figure 4:
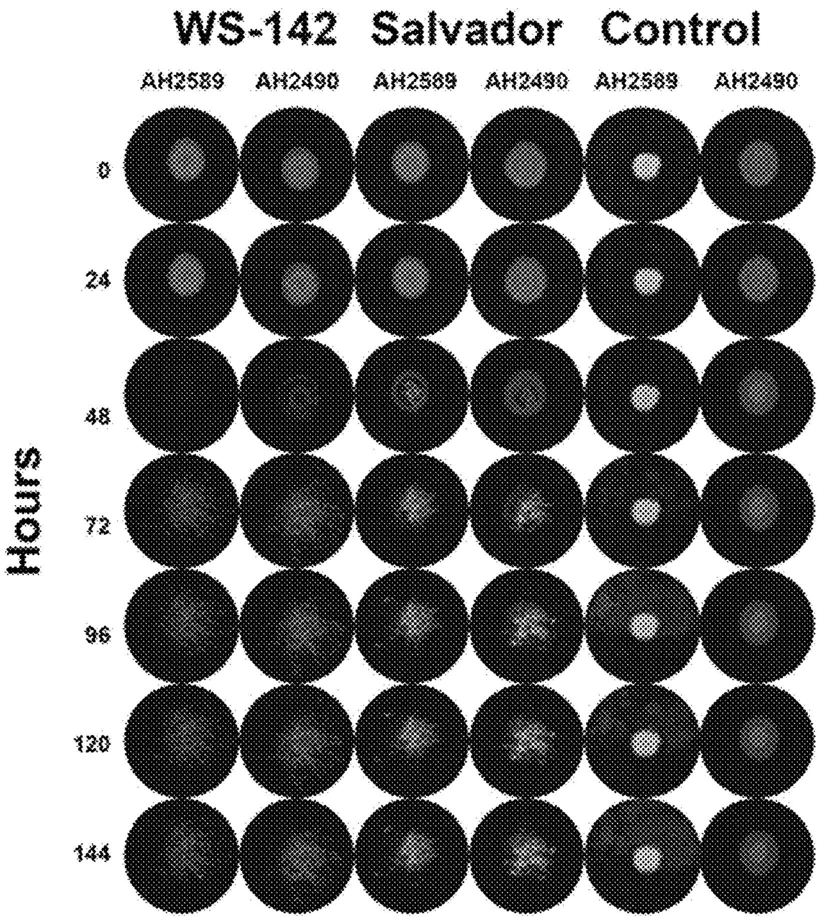
FIG. 4 shows time-lapse imaging of colony destruction by dictyostelids (PpS and WI-142) of biofilm-proficient (AH2490) and biofilm-deficient (AH2589) strains of Se.

The results shown in FIG. 4 demonstrates strains of Dicty (PpS and WS-142) feeding on biofilm proficient (AH2490) and biofilm-deficient Dicty strain (AH2589 ica::dhfr). It is clear from this time-lapse experiment that a colony erosion by amoebae of PpS and WS-142 and beginning of sporulation both occur approximately at the same time for strains AH2490 and AH2589, indicating that EPS presence does not significantly reduce the rate of grazing and phagocytosis in those specific examples of prey-predator assemblage. Thus, both Dicty strains produce and secrete proteases.

Example 2

Dictyostelids feed through phagocytosis. As noted, biofilms are generally believed to be an effective defense mechanism against predation by amoebae because the amoebae cannot engulf big chunks of biofilms, and it is hard to mechanically break biofilms into small digestible pieces (Matz C, Kjelleberg S. Trends Microbiol. 2005; 13(7):302-7). Two other principal properties of the EPS have been noted that appear to contribute to resistance of biofilms to phagocytic predation (Matz C, Kjelleberg S. Trends Microbiol. 2005; 13(7):302-7). First, biofilms chemically interfere with phagocytic activity—the EPS acts as a diffusional road-block for the powerful antibacterials sent by the predatory macrophages. Third, the EPS may "hide" bacterial antigens recognized by phagocytes, interfering with receptor-mediated recognition of a prey particle (Celli J, Finlay B B. Trends in microbiology. 2002; 10(5):232-7.) Furthermore, the EPS matrix may participate in a variety of potential chemical defense mechanisms that could neutralize phagocytes.

Given that Dicty (strain X3 of *Dictyostelium discoideum*) has been shown to secrete a plethora of proteins throughout its development, it is contemplated that other disctyostelids such as PpS may also profusely secrete proteins and use enzymatic activity of some to disperse biofilms, dislodge bacteria to ingest them shortly thereafter. There may also be evolutionarily advantageous to preemptively secrete compounds that delay or prevent biofilm formation from planktonic cultures to facilitate grazing and phagocytosis of bacterial prey.

Figure 5:
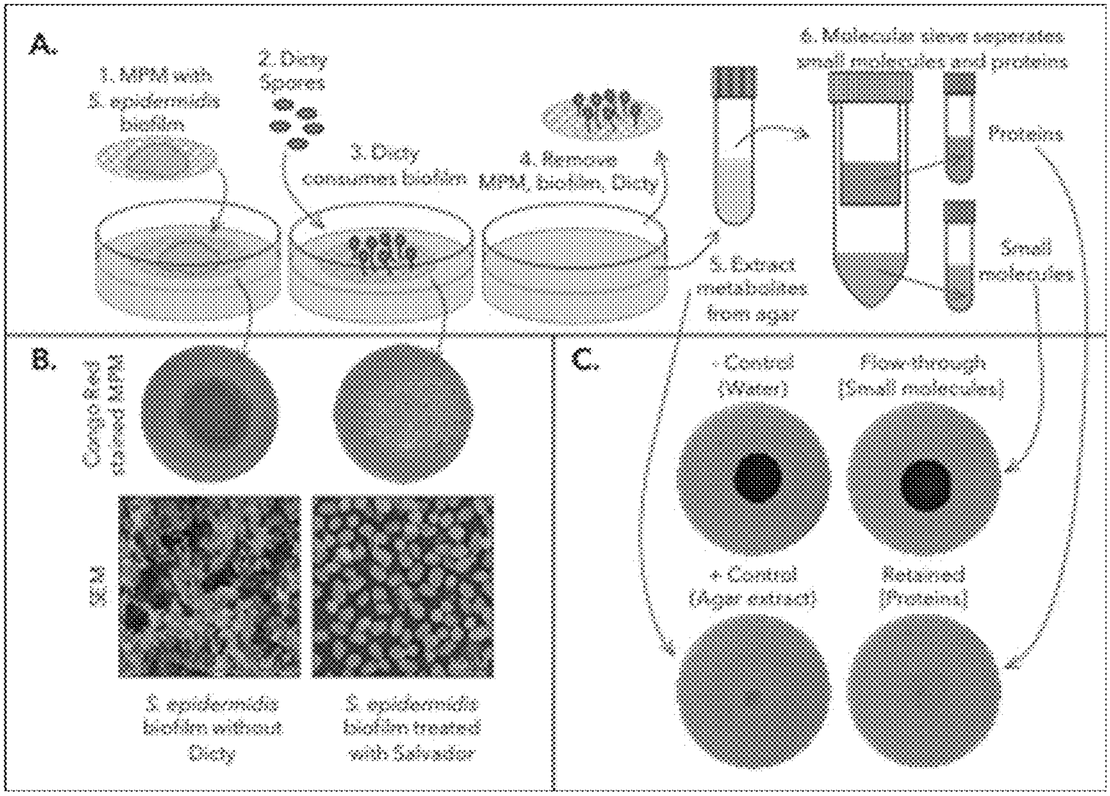
FIG. 5 shows a schematic of an exemplary method for testing DSBD-like molecule production by Dicty with results from PpS. (A) experimental setup for collection of secreted products. (B) data showing dissecting (top) and SEM (bottom) micrographs of MPMs with Se, without and with PpS. Membranes were stained with Congo Red to better show polysaccharide EPS. (C) Application of whole metabolite extract as well as the large-molecule fraction shows biofilm destruction activity. Small molecule fraction, like water-only control, does not disrupt the biofilm. MPMs are stained with Congo Red to better show polysaccharide EPS.

This hypothesis was tested using strain Se that forms exceptionally stable biofilms. Biofilm formation (presence of EPS) was confirmed by using Scanning Electron Microscopy (SEM) (FIG. 5 B bottom). While developing the assays for secreted protein production, it was recognized that the physical separation of the predator/prey assemblage (Dicty and bacteria) from the underlying agar surface is imperative to capture the products secreted and released by feeding predators and dying prey. The use of agar-medium solidified in 6-24-well plates format combined with a microporous filter (0.2 micron) laying atop allowed one to seed bacteria at a medium and at a temperature suitable for biofilm formation. Afterward, the filter was transferred into another multi-well plate containing agar medium conducive to Dicty spore germination, phagocytic feeding of biofilm-enmeshed cells, and their aggregation and multicellular development. As the Dicty feed on a bacterial biofilm pre-formed on the microporous membrane, soluble factors that are produced diffuse into the lower compartment, a well containing a water agar, while organismal components remain on the filter.

Figure 6:
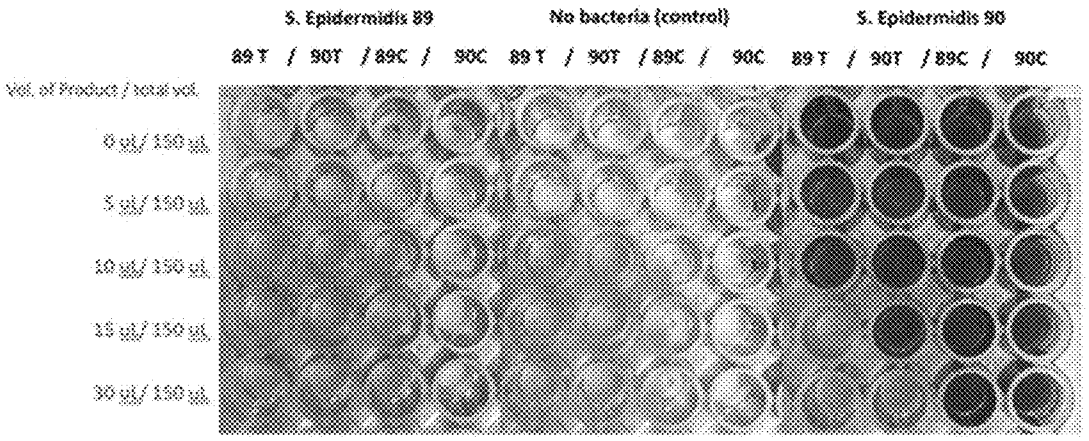
FIG. 6 shows a biofilm-disruption assay using clear-bottomed 96-well cell culture plates. To facilitate detection, readouts are based on crystal violet staining (Merritt et al., Current Protocols in Microbiology. 2005; Chapter 1: Unit1B.) A plate reader is then used to quantitate biofilm formation and breakdown by Dicty products based on the number of bacterial cells attached to substrate.

Upon biofilm colony destruction, Polycarbonate filters were discarded, agar was crushed with sterile spatula, frozen at −20° C. Incubated overnight, thawed on ice and span at 4° C. at 10,000 rpm. The top aqueous phase was harvested and examined for sterility (lack of bacteria and PpS phagocytes). Components accumulated under the filter were re-evaluated after filtration through membranes with a molecular weight cutoff (3 kDa) to determine whether large molecules such as proteins or 2° metabolites are the biofilm antagonists. Those antibiofilm assays were done using another series of polycarbonate filters with preformed Se biofilms (FIG. 5). Robust activity was observed within 6 hours (FIGS. 5 and 6). It was observed that the active agent is proteinaceous. The data indicate that antibiofilm activities purify in two discrete peaks; one exhibiting protease another exopolysaccharide activity.

These proteins are purified to homogeneity using size exclusion and ion exchange chromatography followed by SDS PAGE. Most abundant/active proteins are excised from the gel, proteolytically cleaved and analyzed by Mass spectrometry.

Example 3

A further assay was carried out in clear-bottomed 96-well cell culture plates. To facilitate detection, readouts were based on crystal violet staining (Merritt J H, et al., Current Protocols in Microbiology. 2005; Chapter 1:Unit 1B). A plate reader was used to quantitate biofilm formation based on the number of bacterial cells attached to substrate (FIG. 6). The following procedure was adopted:

Sterile microtiter plates filled with 100 μl of the TSB/D medium per well were inoculated with the Se strain and incubated over night at 37 C with shaking. Four small trays were set up each containing 2 inches of tap water in last three trays. The first tray was used to collect waste, while the other three trays are used to wash the assay plates as described (Merritt J H, et al., supra). The contents of each well were briefly mixed by pipetting, and then 125 μl of the crystal violet/acetic acid solution from each well was transferred to a separate well in an optically clear flat-bottom 96-well plate. The optical density (OD) of each of these 125-μl samples was measured at a wavelength of 500 to 600 nm.

The microtiter biofilm assay provided qualitative results to indicate that Se AH2589 forms much weaker biofilms in comparison to Se AH2490 in TSB/D medium. This is evidenced by the minimal staining of the former strain as compared to the latter strain (FIG. 6). Quantitative analyses were also conducted of the microtiter assay by performing T-tests. The means of the absorbance on TSB/D for Se AH 2589 and AH2490 were 0.086 absorbance units (Au) and 0.128Au, respectively. The p-values obtained from comparing the two strains of bacteria on TSB/D were 0.1056.

Example 4

This example describes degradation of *S. epidermidis* biofilm by Dicty (*Polysphondylium pallidum*)-derived antibiofilm compounds (D-DABC).

Figure 7:
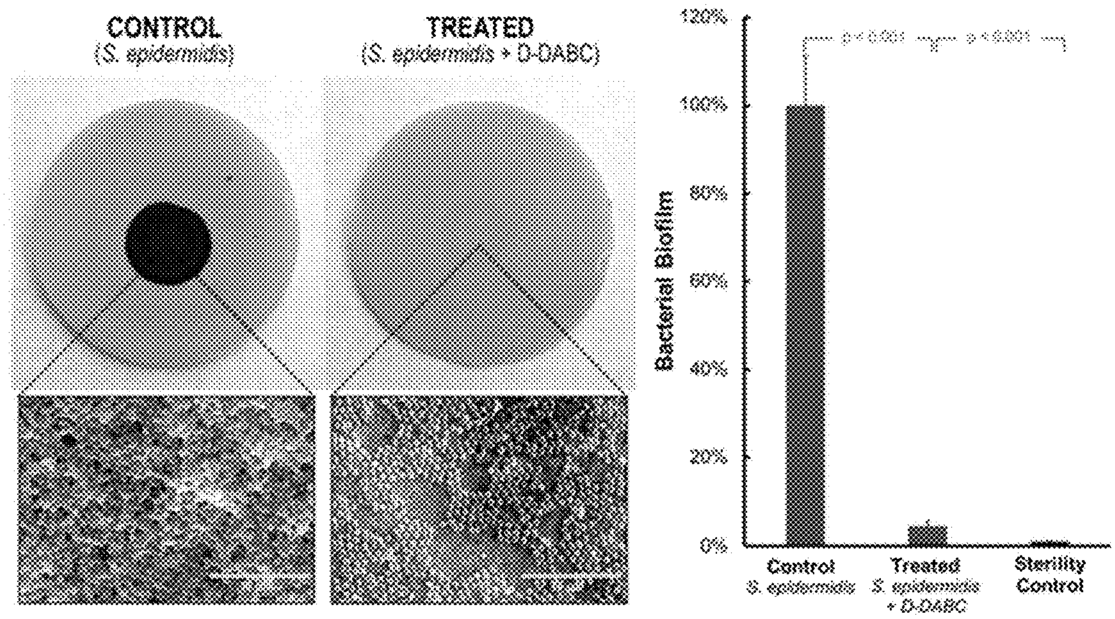
FIG. 7 shows degradation of *S. epidermidis* biofilm by Dicty (*Polysphondylium pallidum*)-derived antibiofilm compounds (D-DABC). Left: images of degradation of biofilms grown on polycarbonate membranes. Right: Quantitation of degradation of biofilms determined using a 96-well microplate assay.

*S. epidermidis* culture was grown overnight at 37° C. with orbital shaking in tryptic soy broth with 1% glucose and added to polycarbonate membranes placed on tryptic soy agar with 1% glucose before incubation for 48 hours to develop biofilms on the membranes. Biofilm membranes were placed on potassium buffer agar and D-DABC solutions were added before incubation overnight at 28° C. Following treatment, biofilm membranes were gently washed with deionized water and stained by application to agar containing Congo red dye. Results are shown in the left, top panel of FIG. 7. *S. epidermidis* biofilms were grown on microporous polycarbonate membrane (MPM) discs and incubated with vehicle (CONTROL) or proteinaceous D-DABC (TREATED) overnight, gently washed to remove non-adhered cells and stained with Congo Red. Exposure to D-DABC produced macroscopically complete removal of biofilm.

Biofilms grown on polycarbonate membranes and treated overnight as described above were fixed with phosphate buffered formalin and dried by stepwise addition of ethanol before critical point drying with carbon dioxide. Dried biofilms were coated with 5 nm of Iridium before imaging with a Hitachi S3400N variable pressure scanning electron microscope. Results are shown in the left, bottom of FIG. 7. Scanning electron microscopy of the MPM discs confirmed the above observations. D-DABC treated biofilm only show sparse monolayer of *S. epidermidis* cells remaining.

*S. epidermidis* culture was grown overnight at 37° C. with orbital shaking in tryptic soy broth with 1% glucose and was diluted to the McFarland standard (~0.1 absorbance at 620 nm) and added to interior wells of a tissue culture-treated, flat-bottom 96-well microplate and incubated at 37° C. overnight with gentle shaking to develop biofilms on the bottom of each well. Media was subsequently removed and D-DABC (at native concentration) was added for overnight incubation at 37° C. with gentle shaking. The D-DABC solution was then removed and wells rinsed with buffer before staining remaining biofilm biomass with 0.1% (w/v) crystal violet dye followed by 3 additional washes with deionized water to remove unbound dye. Crystal violet dye bound to biofilms was solubilized by 30% (v/v) acetic acid and quantified by absorbance at 590 nm. Result are shown in the right panel of FIG. 7. A high-throughput 96-well microplate assay developed to quantitatively assess antibiofilm activity further confirmed the above findings. The assay indicates that the bacterial biofilm is reduced to levels similar to the negative control ("sterility control").

Example 5

This example describes concentration-dependent degradation of *S. epidermidis* biofilm by D-DABC.

Figure 8:
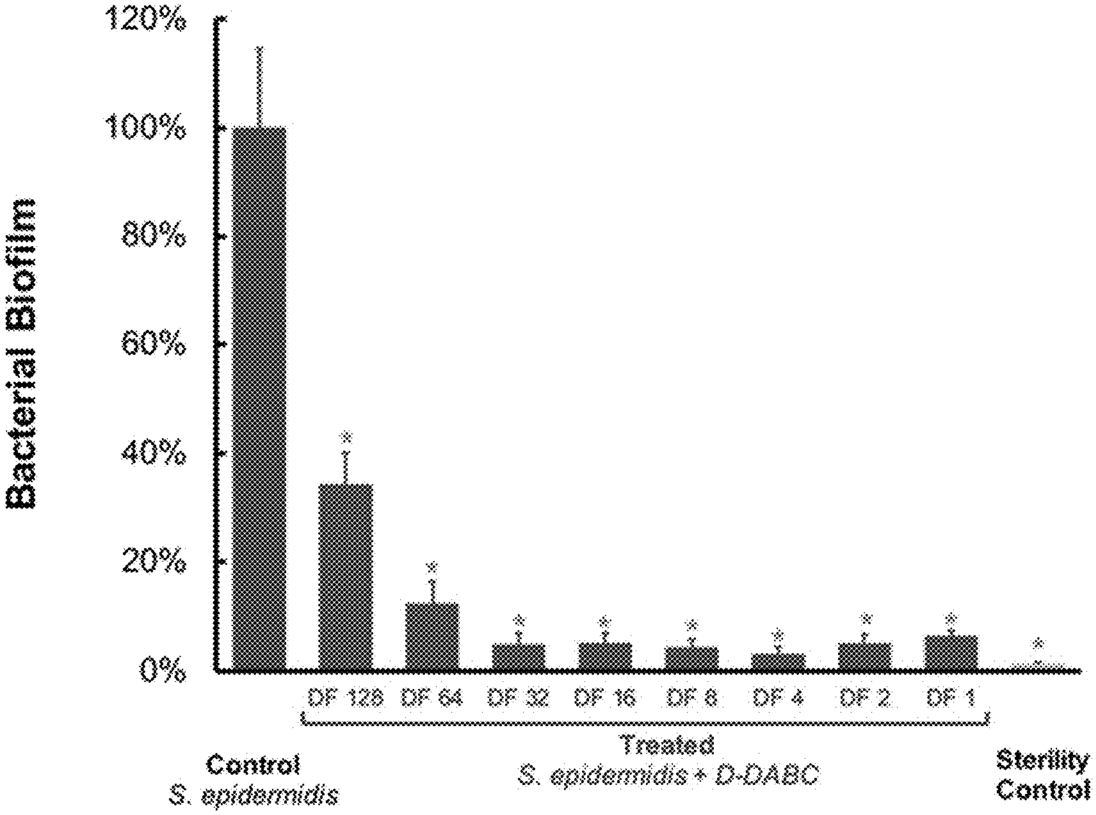
FIG. 8 shows concentration-dependent degradation of *S. epidermidis* biofilm by D-DABC.

*S. epidermidis* culture was grown overnight at 37° C. with orbital shaking in tryptic soy broth with 1% glucose and was diluted to the McFarland standard (~0.1 absorbance at 620 nm) and added to interior wells of a tissue culture-treated, flat-bottom 96-well microplate and incubated at 37° C. overnight with gentle shaking to develop biofilms on the bottom of each well. Media was subsequently removed and D-DABC at varying concentrations was added for overnight incubation at 37° C. with gentle shaking. D-DABC solutions were then removed and wells rinsed with buffer before staining remaining biofilm biomass with 0.1% (w/v) crystal violet dye followed by 3 additional washes with deionized water to remove unbound dye. Crystal violet dye bound to biofilms was solubilized by 30% (v/v) acetic acid and quantified by absorbance at 590 nm Results are shown in FIG. 8. A high-throughput 96-well microplate assay was utilized to quantitatively assess concentration dependence of antibiofilm activity when the biofilms were incubated with D-DABC at varying dilutions [dilution factor (DF) 1 to 128]. The results indicate that the bacterial biofilm is reduced to in a concentration dependent manner from DF 32-DF 128. D-DABC at higher concentrations (DF 1-DF 16) produced similar near-complete degradation of biofilms. "sterility control" denotes the negative control. Asterisks (*) denote a statistically significant (p<0.001) reduction in biofilm.

Example 6

This example describes antibiofilm activity of proteins isolated from *Polysphondylium pallidum* secretions and resolved on native PAGE gel.

Figure 9:
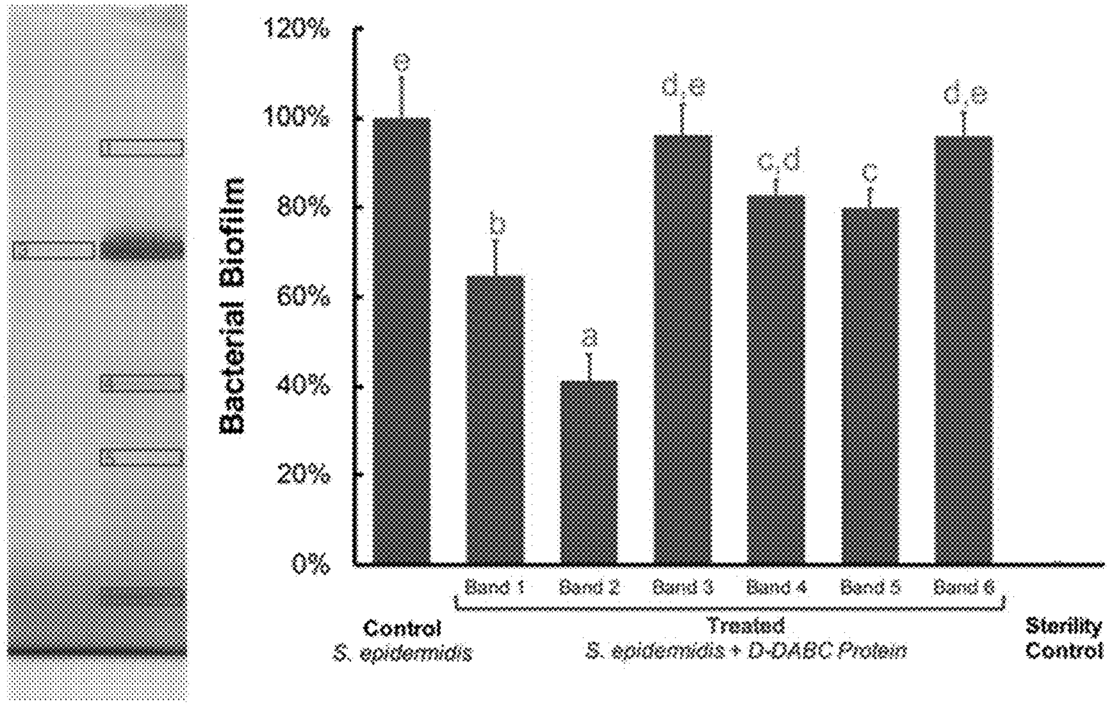
FIG. 9 shows antibiofilm activity of proteins isolated from *Polysphondylium pallidum* secretions and resolved on native PAGE gel.

Liquid recovered from *Polysphondylium pallidum* cultured by adding spores to washed, planktonic *S. epidermidis* cells in potassium phosphate buffer was sterile filtered and fractionated by column chromatography. Fractions having antibiofilm activity were resolved on Native PAGE visualized via Coomassie staining to separate protein components by size (FIG. 9; gel on left). Resulting protein bands were excised from the gel and protein extracted by electroelution. The isolated protein bands were assessed for antibiofilm activity (FIG. 9; right panel) by a crystal violet microplate assay. Protein bands 1, 2, 4 and 5 produced statistically significant degradation of biofilm compared to control (*S. epidermidis* biofilm treated with bovine thrombin, to represent a non-specific protein).

Example 7

This example describes biological safety studies of D-DABC. Liquid recovered from *Polysphondylium pallidum* cultured by adding spores to washed, planktonic *S. epidermidis* cells in potassium phosphate buffer was sterile filtered, and then injected subcutaneously into the back region of pigs. Several days later, the injected region was examined by a board-certified veterinary pathologist. The region was found to be unremarkable; no noticeable signs of inflammation or other acute immune responses were observed.

REFERENCES

1. Sanders D B K, Kisa F. Rakowski S A, Lozano M, Filutowicz M. Multiple dictyostelid species destroy biofilms of *Klebsiella oxytoca* and other Gram negative species. Protist. 2017; 168(3):311-25. doi: doi: 10.1016/j.protis.2017.04.001.
2. Jones T H, de Renobales M, Pon N. Cellulases released during the germination of *Dictyostelium discoideum* spores. Journal of bacteriology. 1979; 137(2):752-7. Epub 1979/02/01. PubMed PMID: 33962; PMCID: 218353.
3. Rosness A. Cellulolytic enzymes during morphogenesis in *Dictyostelium discoideum*. Journal of bacteriology. 1968; 96(3):639-45. Epub 1968 Sep. 1. PubMed PMID: 5753557; PMCID: 252353.
4. Dimond R L, Burns R A, Jordan K B. Secretion of Lysosomal enzymes in the cellular slime mold, *Dictyostelium discoideum*. The Journal of biological chemistry. 1981; 256(13):6565-72. Epub 1981 Jul. 10. PubMed PMID: 7240228.
5. Burns R A, Livi G P, Dimond R L. Regulation and secretion of early developmentally controlled enzymes during axenic growth in *Dictyostelium discoideum*. Developmental biology. 1981; 84(2):407-16. Epub 1981 Jun. 1. PubMed PMID: 20737879.
6. Mierendorf R C, Jr., Cardelli J A, Dimond R L. Pathways involved in targeting and secretion of a lysosomal enzyme in *Dictyostelium discoideum*. J Cell Biol. 1985; 100(5):1777-87. Epub 1985 May 1. PubMed PMID: 3988807; PMCID: 2113895.
7. Bakthavatsalam D, Gomer R H. The secreted proteome profile of developing *Dictyostelium discoideum* cells. Proteomics. 2010; 10(13):2556-9. doi: 10.1002/pmic.200900516. PubMed PMID: 20422638; PMCID: PMC2926150.
8. Eichinger L, Pachebat J A, Glockner G, Rajandream M A, Sucgang R, Berriman M, Song J, Olsen R, Szafranski K, Xu Q, Tunggal B, Kummerfeld S, Madera M, Konfortov B A, Rivero F, Bankier A T, Lehmann R, Hamlin N, Davies R, Gaudet P, Fey P, Pilcher K, Chen G, Saunders D, Sodergren E, Davis P, Kerhomou A, Nie X, Hall N, Anjard C, Hemphill L, Bason N, Farbrother P, Desany B, Just E, Morio T, Rost R, Churcher C, Cooper J, Haydock S, van Driessche N, Cronin A, Goodhead I, Muzny D, Mourier T, Pain A, Lu M, Harper D, Lindsay R, Hauser H, James K, Quiles M, Madan Babu M, Saito T, Buchrieser C, Wardroper A, Felder M, Thangavelu M, Johnson D, Knights A, Loulseged H, Mungall K, Oliver K, Price C, Quail M A, Urushihara H, Hernandez J, Rabbinowitsch E, Steffen D, Sanders M, Ma J, Kohara Y, Sharp S, Simmonds M, Spiegler S, Tivey A, Sugano S, White B, Walker D, Woodward J, Winckler T, Tanaka Y, Shaulsky G, Schleicher M, Weinstock G, Rosenthal A, Cox E C, Chisholm R L, Gibbs R, Loomis W F, Platzer M, Kay R R, Williams J, Dear P H, Noegel A A, Barrell B, Kuspa A. The genome of the social amoeba *Dictyostelium discoideum*. Nature. 2005; 435(7038):43-57. Epub 2005 May 6. doi: nature03481 [pii]10.1038/nature03481. PubMed PMID: 15875012.
9. Sucgang R, Kuo A, Tian X, Salerno W, Parikh A, Feasley C L, Dalin E, Tu H, Huang E, Barry K, Lindquist E, Shapiro H, Bruce D, Schmutz J, Salamov A, Fey P, Gaudet P, Anjard C, Babu M M, Basu S, Bushmanova Y, van der Wel H, Katoh-Kurasawa M, Dinh C, Coutinho P M, Saito T, Elias M, Schaap P, Kay R R, Henrissat B, Eichinger L, Rivero F, Putnam N H, West C M, Loomis W F, Chisholm R L, Shaulsky G, Strassmann J E, Queller D C, Kuspa A, Grigoriev I V. Comparative genomics of the social amoebae *Dictyostelium discoideum* and *Dictyostelium purpureum*. Genome biology. 2011; 12(2):R20. Epub 2011 Mar. 2. doi: 10.1186/gb-2011-12-2-r20. PubMed PMID: 21356102.
10. Heidel A J, Lawal H M, Felder M, Schilde C, Helps N R, Tunggal B, Rivero F, John U, Schleicher M, Eichinger L, Platzer M, Noegel A A, Schaap P, Glockner G. Phylogeny-wide analysis of social amoeba genomes highlights ancient origins for complex intercellular communication. Genome Research. 2011;

21(11):1882-91. Epub 2011 Jul. 16. doi: 10.1101/gr.121137.111. PubMed PMID: 21757610; PMCID: 3205573.

11. Walsh C T. Polyketide and nonribosomal peptide antibiotics: modularity and versatility. Science. 2004; 303(5665):1805-10. PubMed PMID: 15031493.
12. Walsh C. Antibiotics: actions, origins, resistance. Walsh C, editor. Washington: American Society for Microbiology (ASM); 2003. x+335 p.
13. Comillon S, Gebbie L, Benghezal M, Nair P, Keller S, Wehrle-Haller B, Charette S J, Bruckert F, Letourneur F, Cosson P. An adhesion molecule in free-living *Dictyostelium* amoebae with integrin beta features. EMBO reports. 2006; 7(6):617-21. Epub 2006 May 16. doi: 10.1038/sj.embor.7400701. PubMed PMID: 16699495; PMCID: 1479592.
14. Nair D R, Anand, S., Verma, P., Mohanty, D, and R. S. Gokhale. Genetic, biosyntetic and functional versatility of polyketide synthases. Current Science. 2012; 102(2):277-87.
15. Schaap P, Winckler T, Nelson M, Alvarez-Curto E, Elgie B, Hagiwara H, Cavender J, Milano-Curto A, Rozen D E, Dingermann T, Mutzel R, Baldauf S L. Molecular phylogeny and evolution of morphology in the social amoebas. Science. 2006; 314:661-3. PubMed PMID: Pmid: 17068267.
16. Pye C R, Bertin M J, Lokey R S, Gerwick W H, Linington R G. Retrospective analysis of natural products provides insights for future discovery trends. Proc Natl Acad Sci USA. 2017; 114(22):5601-6. doi: 10.1073/pnas.1614680114. PubMed PMID: 28461474; PMCID: PMC5465889.
17. Raper K B, Rahn A W. The dictyostelids. Princeton, N.J.: Princeton University Press; 1984. x, 453 p. p.
18. Shih P C, Huang C T. Effects of quorum-sensing deficiency on *Pseudomonas aeruginosa* biofilm formation and antibiotic resistance. J Antimicrob Chemother. 2002; 49(2):309-14. PubMed PMID: 11815572.
19. Davies J. Resistance redux. Infectious diseases, antibiotic resistance and the future of mankind. EMBO Rep. 2008; 9 Suppl 1:S18-21. PubMed PMID: 18578018.
20. Davies D. Understanding biofilm resistance to antibacterial agents. Nature reviews Drug discovery. 2003; 2(2):114-22. Epub 2003 Feb. 4. doi: 10.1038/nrd1008. PubMed PMID: 12563302.
21. Lynch A S, Robertson G T. Bacterial and fungal biofilm infections. Annual review of medicine. 2008; 59:415-28. doi: 10.1146/annurev.med.59.110106.132000. PubMed PMID: 17937586.
22. Rasmussen T B, Givskov M. Quorum-sensing inhibitors as anti-pathogenic drugs. Int J Med Microbiol. 2006; 296(2-3):149-61. doi: 10.1016/j.ijmm.2006.02.005. PubMed PMID: 16503194.
23. Rosenthal V D, Bijie H, Maki D G, Mehta Y, Apisarnthanarak A, Medeiros E A, Leblebicioglu H, Fisher D, Alvarez-Moreno C, Khader I A, Del Rocio Gonzalez Martinez M, Cuellar L E, Navoa-Ng J A, Abougal R, Guanche Garcell H, Mitrev Z, Pirez Garcia M C, Hamdi A, Duenas L, Cancel E, Gurskis V, Rasslan O, Ahmed A, Kanj S S, Ugalde O C, Mapp T, Raka L, Yuet Meng C, Thu le T A, Ghazal S, Gikas A, Narvaez L P, Mejia N, Hadjieva N, Gamar Elanbya M O, Guzman Siritt M E, Jayatilleke K, members I. International Nosocomial Infection Control Consortium (INICC) report, data summary of 36 countries, for 2004-2009. Am J Infect Control. 2012; 40(5):396-407. doi: 10.1016/j.ajic.2011.05.020. PubMed PMID: 21908073.
24. Kang C I, Kim S H, Kim H B, Park S W, Choe Y J, Oh M D, Kim E C, Choe K W. *Pseudomonas aeruginosa* bacteremia: risk factors for mortality and influence of delayed receipt of effective antimicrobial therapy on clinical outcome. Clin Infect Dis. 2003; 37(6):745-51. doi: 10.1086/377200. PubMed PMID: 12955633.
25. Worthington R J, Richards J J, Melander C. Small molecule control of bacterial biofilms. Org Biomol Chem. 2012; 10(37):7457-74. doi: 10.1039/c2ob25835h. PubMed PMID: 22733439; PMCID: PMC3431441.
26. Stewart P S, Costerton J W. Antibiotic resistance of bacteria in biofilms. Lancet. 2001; 358(9276):135-8. PubMed PMID: 11463434.
27. Jensen T, Pedersen S S, Game S, Heilmann C, Hoiby N, Koch C. Colistin inhalation therapy in cystic fibrosis patients with chronic *Pseudomonas aeruginosa* lung infection. J Antimicrob Chemother. 1987; 19(6):831-8. PubMed PMID: 3301785.
28. Staudinger B J, Muller J F, Halldorsson S, Boles B, Angermeyer A, Nguyen D, Rosen H, Baldursson O, Gottfreethsson M, Guethmundsson G H, Singh P K. Conditions associated with the cystic fibrosis defect promote chronic *Pseudomonas aeruginosa* infection. Am J Respir Crit Care Med. 2014; 189(7):812-24. doi: 10.1164/rccm.201312-21420C. PubMed PMID: 24467627; PMCID: PMC4225830.
29. Tielen P, Rosenau F, Wilhelm S, Jaeger K E, Flemming H C, Wingender J. Extracellular enzymes affect biofilm formation of mucoid *Pseudomonas aeruginosa*. Microbiology. 2010; 156(Pt 7):2239-52. Epub 2010 Apr. 3. doi: 10.1099/mic.0.037036-0. PubMed PMID: 20360178.
30. Flemming H C, Wingender J. The biofilm matrix. Nat Rev Microbiol. 2010; 8(9):623-33. doi: 10.1038/nrmicro2415. PubMed PMID: 20676145.
31. Branda S S, Vik S, Friedman L, Kolter R. Biofilms: the matrix revisited. Trends in Microbiology. 2005; 13(1):20-6. Epub 2005 Jan. 11. doi: 10.1016/j.tim.2004.11.006. PubMed PMID: 15639628.
32. Branda S S, Chu F, Kearns D B, Losick R, Kolter R. A major protein component of the *Bacillus subtilis* biofilm matrix. Mol Microbiol. 2006; 59(4):1229-38. doi: 10.1111/j.1365-2958.2005.05020.x. PubMed PMID: 16430696.
33. More T T, Yadav J S, Yan S, Tyagi R D, Surampalli R Y. Extracellular polymeric substances of bacteria and their potential environmental applications. J Environ Manage. 2014; 144:1-25. doi: 10.1016/j.jenvman.2014.05.010. PubMed PMID: 24907407.
34. Boles B R, Horswill A R. Staphylococcal biofilm disassembly. Trends in microbiology. 2011; 19(9):449-55. Epub 2011 Jul. 26. doi: 10.1016/j.tim.2011.06.004. PubMed PMID: 21784640; PMCID: 3164736.
35. Mah T F, O'Toole G A. Mechanisms of biofilm resistance to antimicrobial agents. Trends Microbiol. 2001; 9(1):34-9. PubMed PMID: 11166241.
36. Walker T S, Tomlin K L, Worthen G S, Poch K R, Lieber J G, Saavedra M T, Fessler M B, Malcolm K C, Vasil M L, Nick J A. Enhanced *Pseudomonas aeruginosa* biofilm development mediated by human neutrophils. Infect Immun. 2005; 73(6):3693-701. doi: 10.1128/IAI.73.6.3693-3701.2005. PubMed PMID: 15908399; PMCID: PMC1111839.

37. Chiang W C, Nilsson M, Jensen P O, Hoiby N, Nielsen T E, Givskov M, Tolker-Nielsen T. Extracellular DNA shields against aminoglycosides in *Pseudomonas aeruginosa* biofilms. Antimicrob Agents Chemother. 2013; 57(5):2352-61. doi: 10.1128/AAC.00001-13. PubMed PMID: 23478967; PMCID: PMC3632962.

38. Sutherland I W. The biofilm matrix—an immobilized but dynamic microbial environment. Trends Microbiol. 2001; 9(5):222-7. PubMed PMID: 11336839.

39. Brefeld O. *Dictyostelium mucoroides*. Ein neuer organismus and der verwandschaft der myxomyceten. Abh Seckenberg Naturforsch Ges. 1869; 7:85-107.

40. Raper K B. *Dictyostelium discoideum*, a new species of slime mold from decaying forest leaves. J Agr Res. 1935; 50:135-47.

41. Baldauf S L, Roger A J, Wenk-Siefert I, Doolittle W F. A kingdom-level phylogeny of eukaryotes based on combined protein data. Science. 2000; 290(5493):972-7. Epub 2000/11/04. PubMed PMID: 11062127.

42. Schaap P. Evolutionary crossroads in developmental biology: *Dictyostelium discoideum*. Development. 2011; 138(3):387-96. doi: 10.1242/dev.048934. PubMed PMID: 21205784; PMCID: PMC3014629.

43. Raper K B. Growth and development of *Dictyostelium discoideum* with bacterial associates. J Agr Res. 1937; 55:289-316.

44. Raper K B. Developmental patterns in simple slime molds. Growth. 1941; 5:41-76.

45. Konijn T M, Van De Meene J G, Bonner J T, Barkley D S. The acrasin activity of adenosine-3',5'-cyclic phosphate. Proc Natl Acad Sci USA. 1967; 58(3):1152-4. Epub 1967/09/01. PubMed PMID: 4861307; PMCID: 335761.

46. Jackson S M, Jones E B G. Interactions within biofilms: disruption of biofilm structure by protozoa. Kieler Meeresforsch. 1991; 8:264-8.

47. Matz C, Kjelleberg S. Off the hook—how bacteria survive protozoan grazing. Trends Microbiol. 2005; 13(7):302-7. Epub 2005 Jun. 7. doi: 50966-842X(05)00134-4 [pii]10.1016/j.tim.2005.05.009. PubMed PMID: 15935676.

48. Weitere M, Bergfeld T, Rice S A, Matz C, Kjelleberg S. Grazing resistance of *Pseudomonas aeruginosa* biofilms depends on type of protective mechanism, developmental stage and protozoan feeding mode. Environ Microbiol. 2005; 7(10):1593-601. Epub 2005/09/15. doi: 10.1111/j.1462-2920.2005.00851.x. PubMed PMID: 16156732.

49. Matz C, McDougald D, Moreno A M, Yung P Y, Yildiz F H, Kjelleberg S. Biofilm formation and phenotypic variation enhance predation-driven persistence of *Vibrio cholerae*. Proc Nat Acad Sci of USA. 2005; 102(46):16819-24. Epub 2005 Nov. 4. doi: 10.1073/pnas.0505350102. PubMed PMID: 16267135; PMCID: 1283802.

50. Matz C, Moreno A M, Alhede M, Manefield M, Hauser A R, Givskov M, Kjelleberg S. *Pseudomonas aeruginosa* uses type III secretion system to kill biofilm-associated amoebae. Isme J. 2008; 2(8):843-52. Epub 2008 May 16. doi: 10.1038/ismej.2008.47. PubMed PMID: 18480848; PMCID: 2662702.

51. Sanders D, Borys K D, Kisa F, Rakowski S A, Lozano M, Filutowicz M. Multiple Dictyostelid Species Destroy Biofilms of *Klebsiella oxytoca* and Other Gram Negative Species. Protist. 2017; 168(3):311-25. doi: 10.1016/j.protis.2017.04.001. PubMed PMID: 28499132.

52. Raper K B. *Dictyostelium* polycephalum n. sp.: a new cellular slime mould with coremiform fructifications. J Gen Microbiol. 1956; 14(3):716-32. Epub 1956 Jul. 1. PubMed PMID: 13346033.

53. Jurgens K, Matz C. Predation as a shaping force for the phenotypic and genotypic composition of planktonic bacteria. Antonie Van Leeuwenhoek. 2002; 81(1-4):413-34. Epub 2002/11/27. PubMed PMID: 12448740.

54. Vetsigian K, Jajoo R, Kishony R. Structure and evolution of *Streptomyces* interaction networks in soil and in silico. PLoS Biol. 2011; 9(10):e1001184. Epub 2011 Nov. 1. doi: 10.1371/journal.pbio.1001184. PubMed PMID: 22039352; PMCID: 3201933.

55. Sauer K, Camper A K, Ehrlich G D, Costerton J W, Davies D G. *Pseudomonas aeruginosa* displays multiple phenotypes during development as a biofilm. Journal of bacteriology. 2002; 184(4):1140-54. Epub 2002 Jan. 25. PubMed PMID: 11807075; PMCID: 134825.

56. Fey P D, Olson M E. Current concepts in biofilm formation of *Staphylococcus epidermidis*. Future Microbiol. 2010; 5(6):917-33. doi: 10.2217/fmb.10.56. PubMed PMID: 20521936; PMCID: 2903046.

57. Lawrence J R, Snyder R A. Feeding behaviour and grazing impacts of a Euplotes sp. on attached bacteria. Canadian journal of microbiology. 1998; 44(7):623-9. PubMed PMID: ISI:000076321000002.

58. Choi Y C, Morgenroth E. Monitoring biofilm detachment under dynamic changes in shear stress using laser-based particle size analysis and mass fractionation. Water science and technology: a journal of the International Association on Water Pollution Research. 2003; 47(5):69-76. Epub 2003 Apr. 19. PubMed PMID: 12701909.

59. Ymele-Leki P, Ross J M. Erosion from *Staphylococcus aureus* biofilms grown under physiologically relevant fluid shear forces yields bacterial cells with reduced avidity to collagen. Appl Environ Microb. 2007; 73(6):1834-41. Epub 2007 Feb. 6. doi: 10.1128/AEM.01319-06. PubMed PMID: 17277217; PMCID: 1828840.

60. Curtis T P, Sloan W T, Scannell J W. Estimating prokaryotic diversity and its limits. Proc Natl Acad Sci USA. 2002; 99(16):10494-9. doi: 10.1073/pnas.142680199. PubMed PMID: 12097644; PMCID: PMC124953.

61. Carilla-Latorre S, Calvo-Garrido J, Bloomfield G, Skelton J, Kay R R, Ivens A, Martinez J L, Escalante R. *Dictyostelium* transcriptional responses to *Pseudomonas aeruginosa*: common and specific effects from PAO1 and PA14 strains. BMC Microbiol. 2008; 8:109. Epub 2008 Jul. 2. doi: 10.1186/1471-2180-8-109. PubMed PMID: 18590548; PMCID: 2474670.

62. Sussman M. The origin of cellular heterogeneity in the slime molds, dictyosteliaceae. Journal of Experimental Zoology. 1951; 118(3):407-17. doi: 10.1002/jez.1401180303.

63. Fey P, Kowal A S, Gaudet P, Pilcher K E, Chisholm R L. Protocols for growth and development of *Dictyostelium discoideum*. Nat Protoc. 2007; 2(6):1307-16. Epub 2007 Jun. 5. doi: nprot.2007.178 [pii] 10.1038/nprot.2007.178. PubMed PMID: 17545967.

64. Iranfar N, Fuller D, Loomis W F. Genome-wide expression analyses of gene regulation during early development of *Dictyostelium discoideum*. Eukaryot Cell. 2003; 2(4):664-70. Epub 2003 Aug. 13. PubMed PMID: 12912885; PMCID: PMC178357.

65. Van Driessche N, Shaw C, Katoh M, Morio T, Sucgang R, Ibarra M, Kuwayama H, Saito T, Urushihara H, Maeda M, Takeuchi I, Ochiai H, Eaton W, Tollett J, Halter J, Kuspa A, Tanaka Y, Shaulsky G. A transcriptional profile of multicellular development in *Dictyostelium discoideum*. Development. 2002; 129 (7):1543-52. Epub 2002 Mar. 30. PubMed PMID: 11923193.

66. Serafimidis I, Kay R R. New prestalk and prespore inducing signals in *Dictyostelium*. Dev Biol. 2005; 282(2):432-41. Epub 2005 Jun. 14. doi: 50012-1606 (05)00193-4 [pii]10.1016/j.ydbio.2005.03.023. PubMed PMID: 15950608.

67. Zucko J, Skunca N, Curk T, Zupan B, Long P F, Cullum J, Kessin R H, Hranueli D. Polyketide synthase genes and the natural products potential of *Dictyostelium discoideum*. Bioinformatics. 2007; 23(19):2543-9. Epub 2007 Jul. 31. doi: btm381 [pii]10.1093/bioinformatics/btm381. PubMed PMID: 17660200.

68. Merritt R I, Kadouri D E, O'Toole G A. Growing and analyzing static biofilms. Current Protocols in Microbiology. 2005; Chapter 1:Unit 1B Epub 2008 Sep. 5. doi: 10.1002/9780471729259.mc01b01s00. PubMed PMID: 18770545.

69. Zhang R I, Chung T D, Oldenburg K R. A simple statistical parameter for use in evaluation and validation of high throughput screening assays. J Biomol Screen. 1999; 4(2):67-73. PubMed PMID: 10838414.

70. Zhao T, Liu Y. N-acetylcysteine inhibit biofilms produced by *Pseudomonas aeruginosa*. BMC Microbiol. 2010; 10:140. doi: 10.1186/1471-2180-10-140. PubMed PMID: 20462423; PMCID: PMC2882372.

71. Singh P K, Parsek M R, Greenberg E P, Welsh M J. A component of innate immunity prevents bacterial biofilm development. Nature. 2002; 417(6888):552-5. doi: 10.1038/417552a. PubMed PMID: 12037568.

72. Cowan S D L, and J Keasling. Development of engineered biofilms on poly-L-Lysine patterned surfaces. Biotechnology letters. 2001; 23(15):1235-41.

73. Ceri H, Olson M E, Stremick C, Read R R, Morck D, Buret A. The Calgary Biofilm Device: New technology for rapid determination of antibiotic susceptibilities of bacterial biofilms. Journal of Clinical Microbiology. 1999; 37(6):1771-6. PubMed PMID: ISI: 000080344900019.

All publications and patents mentioned in the above specification are herein incorporated by reference. Various modifications and variations of the described method and system of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure which are obvious to those skilled in the relevant fields are intended to be within the scope of the following claims.

We claim:

1. A method of treating a *Staphylococcus epidermidis* biofilm accumulation, comprising:

culturing *Polysphondylium pallidum* amoebae in the presence of *Staphylococcus epidermidis* bacteria to provide a culture medium comprising a secretome from the *Polysphondylium pallidum;* removing the *Polysphondylium pallidum* amoebae from the culture medium comprising the secretome to obtain an amoebae-free medium comprising the secretome;

isolating proteins or proteins and small molecules from the amoebae-free medium comprising the secretome using filtration and/or chromatography to provide a fraction of the secretome comprising the proteins or the proteins and the small molecules; and contacting the *Staphylococcus epidermidis* biofilm with the fraction of the secretome comprising the proteins or the proteins and the small molecules, thereby treating the *Staphylococcus epidermidis* biofilm.

2. The method of claim 1, wherein said chromatography comprises a) contacting said amoebae-free medium comprising the secretome with an anion exchange resin in a low ionic strength buffer; and b) eluting said proteins with a high ionic strength buffer.

3. The method of claim 2, wherein said high ionic strength buffer comprises 250 mM NaCl.

4. The method of claim 2, further comprising the step of washing said column with a buffer comprising 150 mM NaCl prior to said eluting.

5. The method of claim 1, wherein said biofilm is in or on a surface or on a subject.

6. The method of claim 1, wherein said *Polysphondylium pallidum* amoebae is *Polysphondylium pallidum* Salvador.

7. The method of claim 1, wherein said composition further comprises a non-amoebae anti-microbial agent.

8. A method of treating a subject infected with a *Staphylococcus epidermidis* biofilm, comprising:

culturing *Polysphondylium pallidum* amoebae in the presence of *Staphylococcus epidermidis* bacteria to provide a culture medium comprising a secretome from the *Polysphondylium pallidum;* removing the *Polysphondylium pallidum* amoebae from the culture medium comprising the secretome to obtain an amoebae-free medium comprising the secretome;

isolating proteins or proteins and small molecules from the amoebae-free medium comprising the secretome using filtration and/or chromatography to provide a fraction of the secretome comprising the proteins or the proteins and the small molecules; and contacting the subject infected with the *Staphylococcus epidermidis* biofilm with the fraction of the secretome comprising the proteins or the proteins and the small molecules, thereby treating the subject infected with the *Staphylococcus epidermidis* biofilm.

9. The method of claim 8, wherein said subject is a human.

10. A method of preventing a *Staphylococcus epidermidis* biofilm accumulation on a device, comprising:

culturing *Polysphondylium pallidum* amoebae in the presence of Staphylococcus epidermidis bacteria to provide a culture medium comprising a secretome from the *Polysphondylium pallidum;* removing the *Polysphondylium pallidum* amoebae from the culture medium comprising the secretome to obtain an amoebae-free medium comprising the secretome;

isolating proteins or proteins and small molecules from the amoebae-free medium comprising the secretome using filtration and/or chromatography to provide a fraction of the secretome comprising the proteins or the proteins and the small molecules; and contacting the device with the fraction of the secretome comprising the proteins or the proteins and the small molecules, thereby preventing the *Staphylococcus epidermidis* biofilm accumulation on the device.

* * * * *